(12) United States Patent
Jarrett et al.

(10) Patent No.: US 12,226,341 B2
(45) Date of Patent: Feb. 18, 2025

(54) IMPLANT INJECTOR DEVICE

(71) Applicant: OCULAR THERAPEUTIX, INC., Bedford, MA (US)

(72) Inventors: Peter Jarrett, Burlington, MA (US); Erik Wong, Newton, MA (US); Eric Dickinson, Amherst, NH (US)

(73) Assignee: OCULAR THERAPEUTIX, INC., Bedford, MA (US)

( * ) Notice: Subject to any disclaimer, the term of this patent is extended or adjusted under 35 U.S.C. 154(b) by 0 days.

(21) Appl. No.: 18/282,124

(22) PCT Filed: Mar. 24, 2022

(86) PCT No.: PCT/US2022/021700
§ 371 (c)(1),
(2) Date: Sep. 14, 2023

(87) PCT Pub. No.: WO2022/204374
PCT Pub. Date: Sep. 29, 2022

(65) Prior Publication Data
US 2024/0041647 A1   Feb. 8, 2024

Related U.S. Application Data

(60) Provisional application No. 63/165,536, filed on Mar. 24, 2021.

(51) Int. Cl.
*A61F 9/00* (2006.01)
*A61M 5/158* (2006.01)

(52) U.S. Cl.
CPC .......... *A61F 9/0017* (2013.01); *A61M 5/158* (2013.01)

(58) Field of Classification Search
CPC . A61F 9/0017; A61M 5/329; A61M 37/0069; A61M 2005/31508; A61M 31/007; A61K 9/0051
See application file for complete search history.

(56) References Cited

U.S. PATENT DOCUMENTS

| 11,534,396 | B2 | 12/2022 | Blizzard et al. |
| 2005/0084631 | A1* | 4/2005 | Anderson ............. A61M 5/003 428/34.1 |

(Continued)

FOREIGN PATENT DOCUMENTS

| EP | 3884929 A1 | 9/2021 |
| WO | 2008/033426 A1 | 3/2008 |

OTHER PUBLICATIONS

International Search Report and Written Opinion of International Application No. PCT/US2022/021700 mailed Jun. 24, 2022, 13 pgs.

*Primary Examiner* — Tiffany Legette
(74) *Attorney, Agent, or Firm* — Lowenstein Sandler LLP

(57) ABSTRACT

A system (100) includes a first assembly (110A) and a second assembly (110B). The first assembly (110A) includes a body (120) forming a first interior volume, a plunger (130) comprising a first distal end disposed within the first interior volume, a wire comprising a first distal end secured to the first distal end of the plunger (130), and a plunger clip (140) configured to interface with the plunger (130) and the body (120) to prevent actuation of the plunger (130). The second assembly (110B) includes a cowl (150) forming a second interior volume, a needle comprising a hub and a shaft, and a cowl cap disposed partially within the hub to secure the implant in the shaft. A first distal end of the shaft is connected to the hub. The hub is disposed within the second interior volume. The shaft is configured to receive an implant.

29 Claims, 18 Drawing Sheets

(56) References Cited

U.S. PATENT DOCUMENTS

| | | | |
|---|---|---|---|
| 2008/0071246 A1* | 3/2008 | Nazzaro | A61M 37/0069 604/60 |
| 2010/0255061 A1* | 10/2010 | de Juan, Jr. | A61K 9/0051 604/93.01 |
| 2015/0190279 A1* | 7/2015 | Acharya | A61K 9/7007 604/290 |
| 2015/0202419 A1* | 7/2015 | Wetzel | A61M 37/0069 29/434 |
| 2015/0238687 A1* | 8/2015 | Novakovic | A61M 5/158 604/502 |
| 2019/0336693 A1* | 11/2019 | Orofino | A61M 5/002 |

* cited by examiner

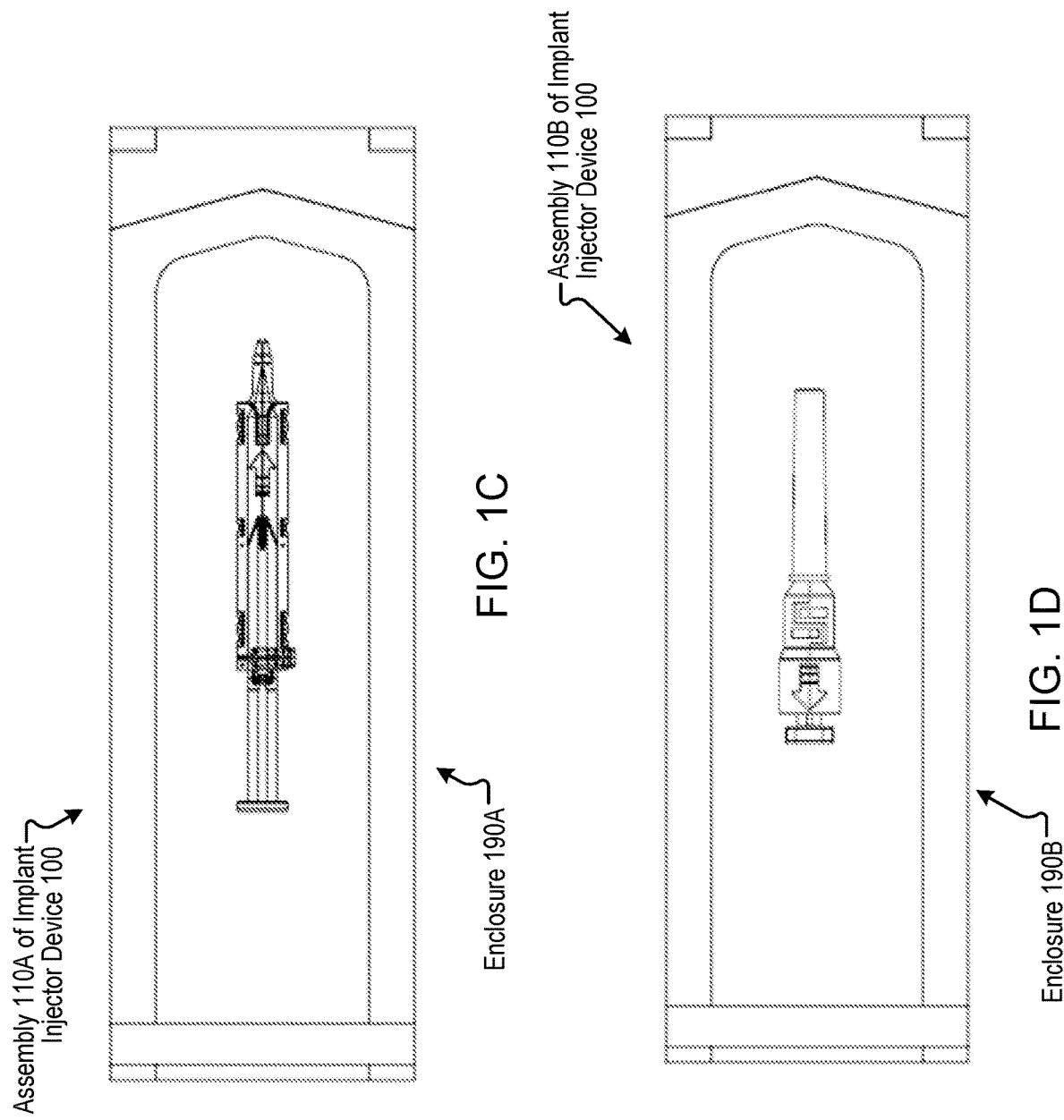

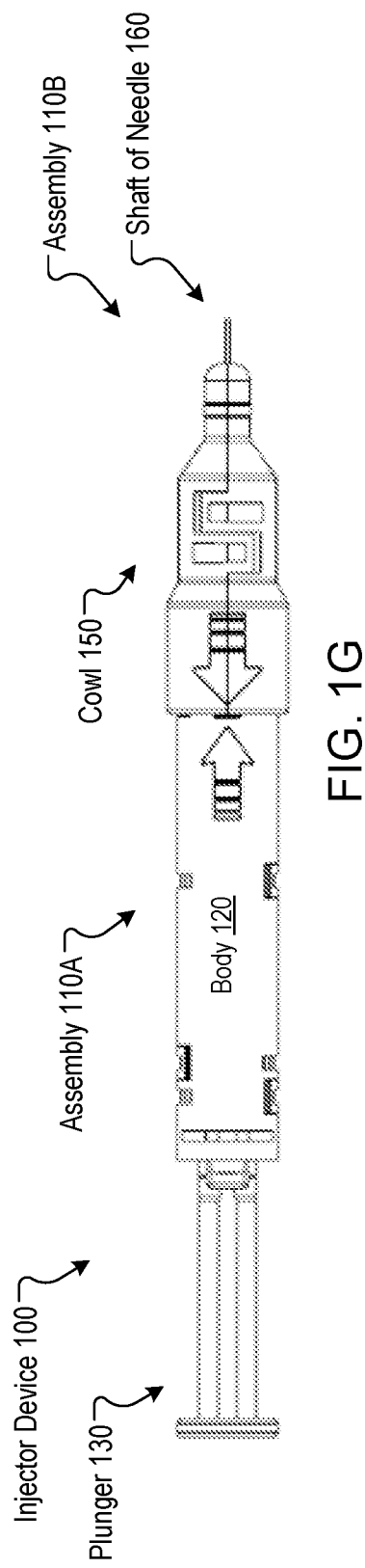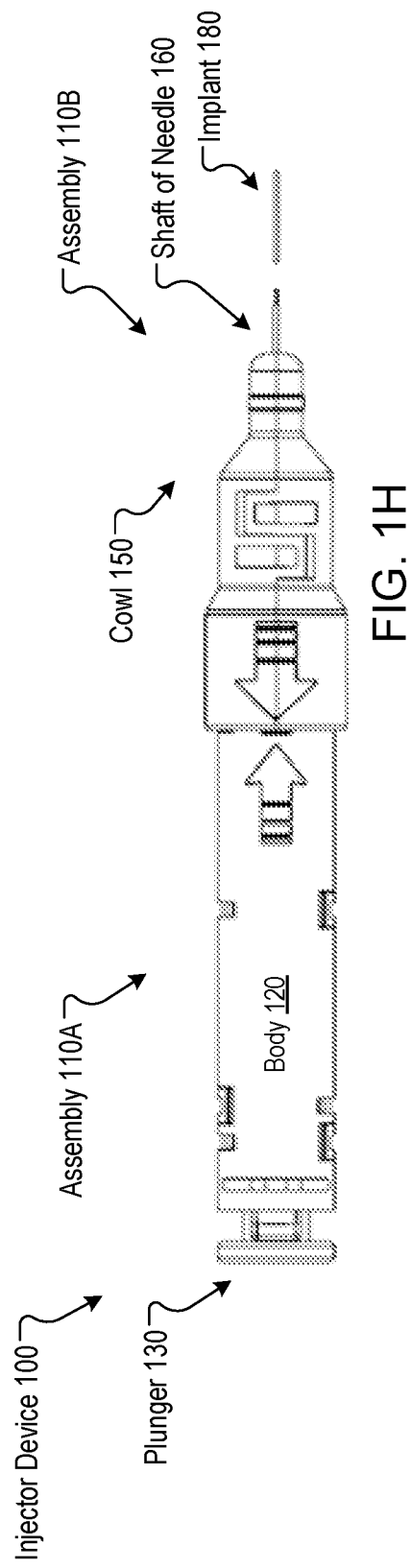
FIG. 1G
FIG. 1H

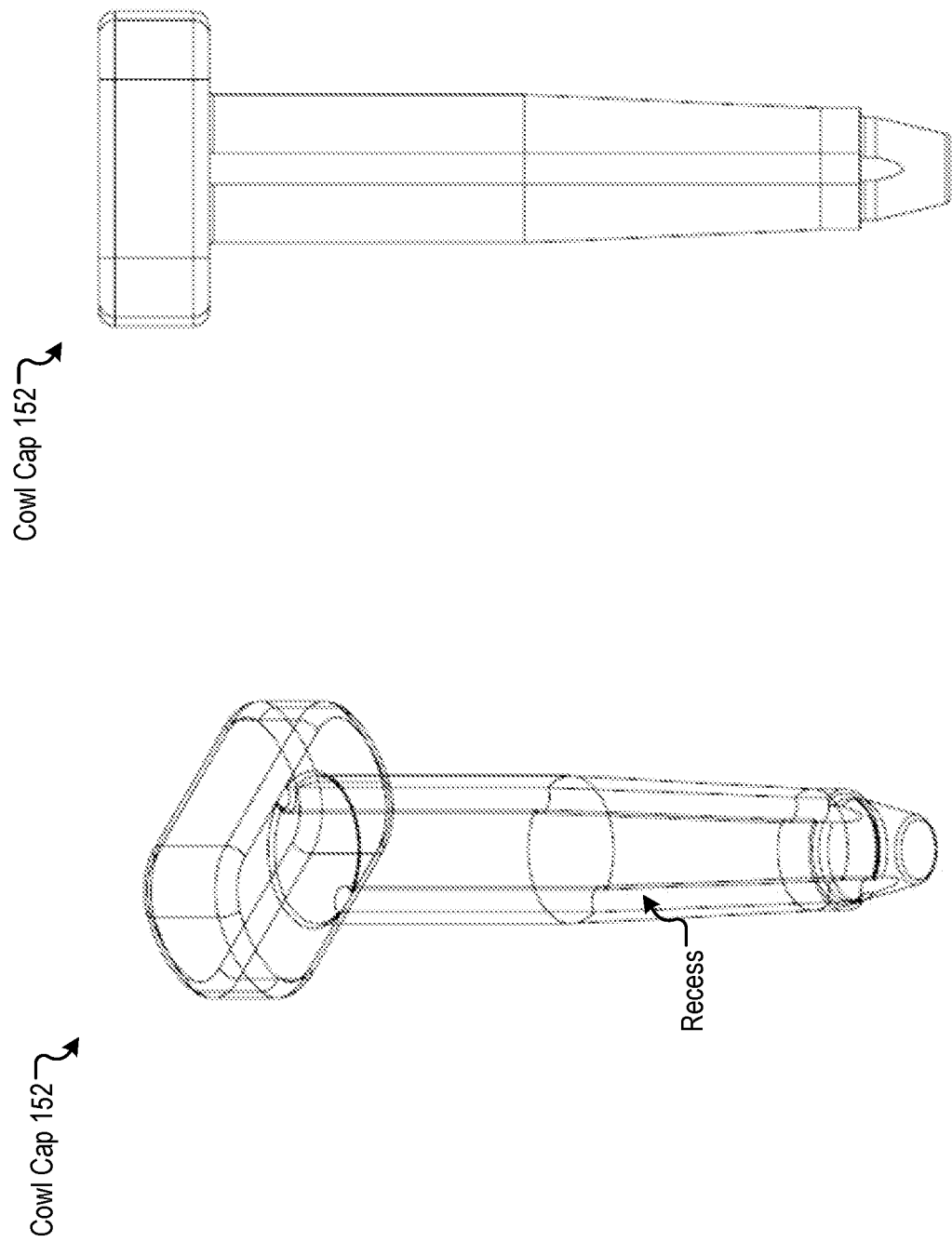

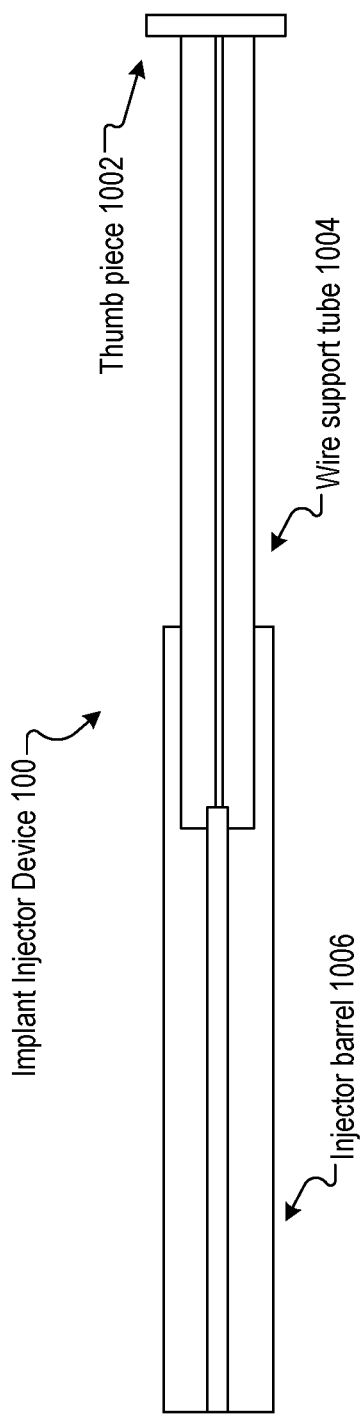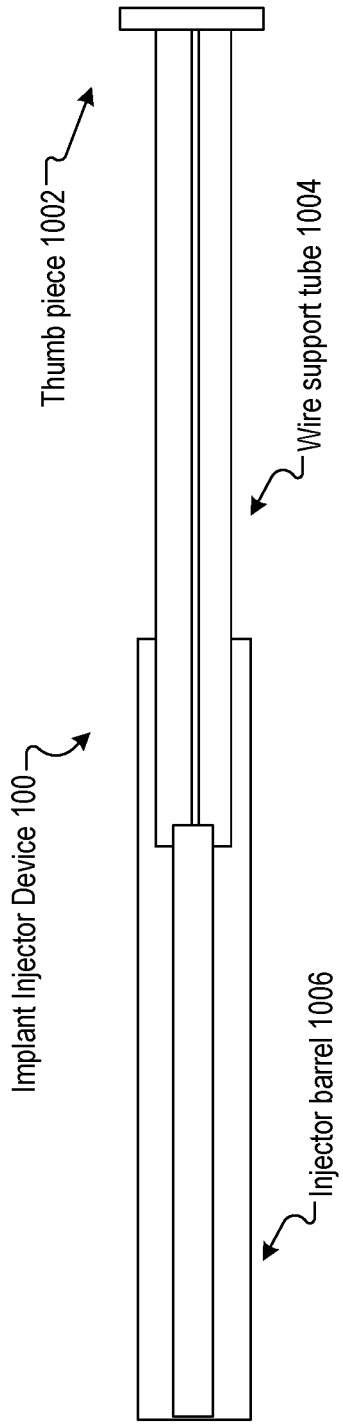
FIG. 10B
FIG. 10C

IMPLANT INJECTOR DEVICE

RELATED APPLICATIONS

This application claims benefit of U.S. Provisional Application No. 63/165,536, filed Mar. 24, 2021, the entire contents of which are incorporated by reference in their entirety and for all purposes.

TECHNICAL FIELD

Embodiments of the present disclosure relate to an injector device, and in particular to an implant injector device.

BACKGROUND

Injectors are used to deploy material, such as implants, into users. An injector can be used to deploy a material into the eye.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIGS. 1A-H illustrate components of implant injector devices, according to certain embodiments.

FIG. 6A-B illustrate a cowl cap of an implant injector device, according to certain embodiments.

FIGS. 10A-C illustrate implant injector devices, according to certain embodiments.

DETAILED DESCRIPTION OF EMBODIMENTS

Figure 1A:
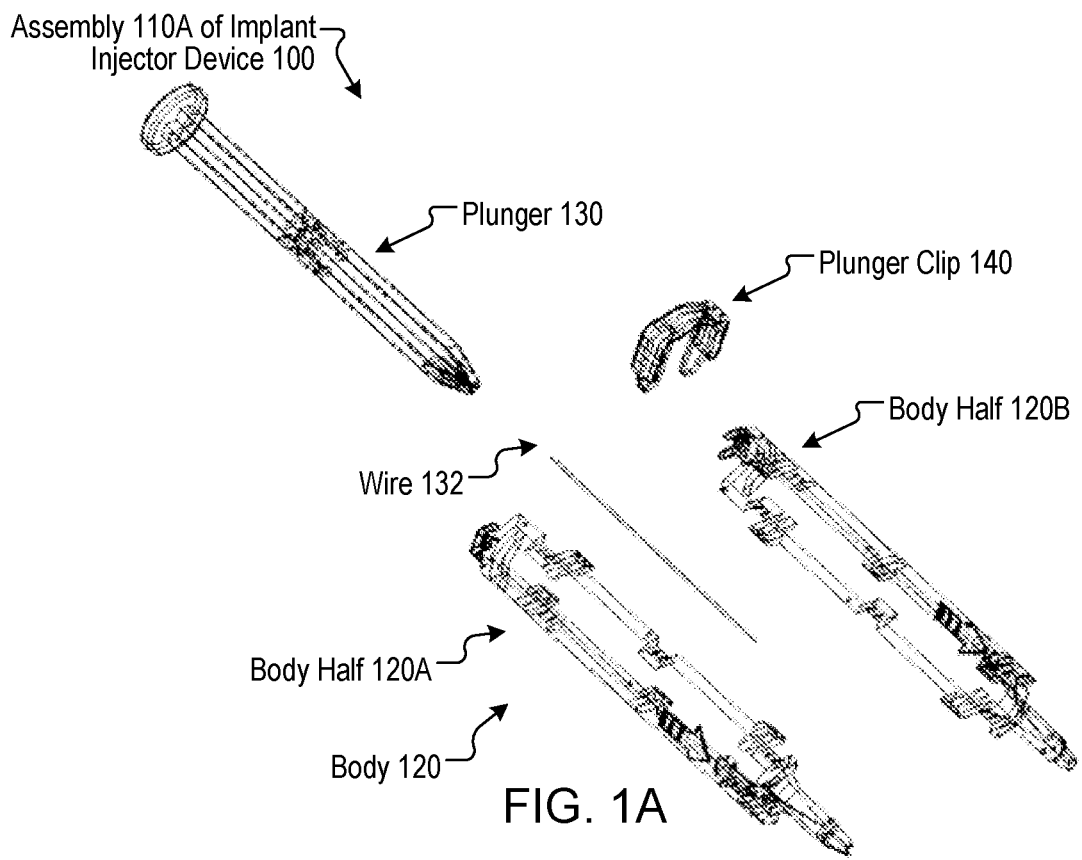

Embodiments described herein are related to implant injector devices.

Injectors are used to deploy material, such as implants, into users. Some material is therapeutic material. Some material is to be deployed at specific locations in a user. Material to be deployed into a user may be sensitive to moisture.

Conventionally, material may be deployed into incorrect locations in a user. For example, an implant may be designed to be deployed into the pars plana of a user and if the implant is not deployed correctly, the implant could impact the back of the retina and cause issues for the user.

Conventionally, material to be deployed into a user may absorb moisture. For example, an implant may absorb moisture from other components of the injector or from the environment. An implant may degrade and/or expand in the presence of moisture which decreases the efficacy of the implant and may prevent insertion of the implant into the user.

Conventionally, assembly of an injector and loading of an implant into an injector by a user is prone to errors. Erroneously loading of an implant and/or erroneously assembling an injector can cause an implant to not be deployed correctly.

Conventionally, deploying of an implant into a user is error prone. For example, an actuating device may be unintentionally pushed into or pulled out of an injector. Unintentionally moving an actuating device may cause errors in deployment of the implant.

The devices, systems, and methods disclosed herein provide an implant injector device.

In some embodiments, the implant injector device includes a first assembly and a second assembly. The first assembly and second assembly may be packaged separately. The first assembly may include a body, a plunger disposed partially within the body, a wire secured to a distal end of the plunger within the body, and a plunger clip configured to prevent actuation of the plunger. The second assembly may include a needle including a hub and a shaft (e.g., tube), a cowl disposed around the needle, a cowl cap (e.g., plug, needle hub plug) disposed partially within the hub to secure the implant in the shaft, and a needle shield secured to the cowl over a portion of the shaft. The second assembly may include an implant disposed in the shaft.

The first assembly may be packaged separately from the second assembly. The second assembly (e.g., with the implant loaded in the second assembly) may be conditioned (e.g., undergo nitrogen conditioning) to remove moisture from the second assembly prior to being packaged. The second assembly may be made of materials that have low moisture content. The first assembly may not undergo conditioning to remove moisture and/or may be made of materials that do not have low moisture content (e.g., be made of more durable materials, etc.). The second assembly may be secured to the first assembly by removing the cowl cap and securing inner protrusions (e.g., of clips) of the cowl to outer recesses of the body.

A distal end of the shaft (e.g., tube) that is to be injected into a user may include a biocompatible material tip (e.g., biocompatible material, biocompatible material plug, polymer tip, polyethylene glycol (PEG) tip) that prevents the implant from falling out of the shaft, prevents moisture from entering the shaft, and prevents coring of tissue (e.g., via the hollow end of the shaft) upon injection. The biocompatible material tip at least partially dissolves responsive to being inserted into a user to allow the implant to be deployed. The biocompatible material tip may not impact the sharpness of the needle and the ability of the needle to penetrate a user.

The body may include a first body half and a second body half that have staggered clips and staggered recesses to interconnect with each other. The first body half and the second body halve may have the same dimensions (e.g., made from the same mold). The plunger clip may have a friction fit or snap fit with the body to prevent the plunger clip from unintentionally falling from the body. The body may include a living hinge to prevent the plunger from unintentionally being actuated and from unintentionally coming out of the body after actuation (e.g., the implant is to be deployed from the shaft responsive to the plunger clip being removed and the plunger being actuated by a first threshold force that is greater than a friction force of one or more living hinges of the body against the plunger). The implant is to be deployed from the shaft responsive to the plunger clip being removed and a living hinge of the body being actuated by the plunger via a first threshold force causing actuation of the plunger The systems, devices, and methods disclosed herein have advantages over conventional solutions. The implant injection device of the present disclosure may have a cowl that only exposes a length of the shaft that corresponds to the specific location of deployment to avoid errors of conventional solutions of deploying implants in incorrect locations. The implant injection device of the present disclosure may include a second assembly housing the implant that is conditioned to remove moisture, packaged separately from the first assembly, and has a biocompatible tip to prevent the implant from being in the presence of moisture to avoid degradation and expansion of implants of conventional solutions. The implant injection device of the present disclosure includes a first assembly and a second assembly that secure to each other via corresponding features to avoid assembly errors of conventional solutions. The implant injection device of the present disclosure includes a plunger clip with a friction fit or a snap fit and a body with a living hinge that avoids errors in deployment of implants of conventional solutions (e.g., the implant is to be deployed from the shaft responsive to the plunger clip being removed and the plunger being actuated by a first threshold force that is greater than a friction force of one or more living hinges of the body against the plunger).

Although certain embodiments of the present disclosure refer to implants to be deployed in the pars plana, embodiments of the present disclosure may be used with one or more objects that are to be inserted into a user. In some embodiments, an object may include one or more of an object to be deployed into a liquid within a user, into fatty tissue within a user, into an eye of a user, and/or the like.

Although certain embodiments of the present disclosure refer to an implant injector device being made from a first assembly and a second assembly that are packaged separately, embodiments of the present disclosure may include an implant injector device that is a single assembly and/or is within a single package.

FIGS. 1A-E illustrate components of implant injector devices 100 (e.g., applicators, plunger-actuated implant injector devices, etc.), according to certain embodiments. In some embodiments, the implant injector device 100 includes assembly 110A (e.g., actuating assembly, see FIGS. 1A and 1C) and assembly 110B (e.g., injector assembly, see FIGS. 1B and 1D). In some embodiments, assembly 110A is packaged in enclosure 190A and assembly 110B is packaged in enclosure 190B (e.g., see FIGS. 1C-D). The enclosures may be peelable foil pouches. In some embodiments, implant injector device 110 is a single assembly and/or is packaged in a single enclosure.

Assembly 110A includes a body 120, a plunger 130, a wire 132 (e.g., push wire secured to the plunger 130 via adhesive such as ultra violet (UV) cure glue), and a plunger clip 140. In some embodiments, the body 120 includes a body half 120A and body half 120B. The body 120 forms an interior volume and a distal end of the plunger 130 is disposed in the interior volume of the body. The wire 132 has a distal end secured to the distal of the plunger 130 within the body 120. The plunger clip 140 is configured to interface with the body 120 and the plunger 130 (e.g., via corresponding slots of the body 120 and the plunger 130) to prevent actuation of the plunger 130 (e.g., prevent pushing plunger 130 further into the body 120 and to prevent pulling plunger 130 further out of the body 120). The wire 132 may be Nitinol, stainless steel, and/or Teflon.

Assembly 110B includes a cowl 150, a needle 160, a cowl cap 152 (e.g., plug, needle hub plug), and a needle shield 170. In some embodiments, the cowl 150 includes a cowl half 150A and cowl half 150B. The needle 160 may include a hub and a shaft (e.g., tube). In some embodiments, the needle 160 has a biocompatible tip 162 secured to the shaft. The cowl 150 forms an interior volume and the hub of the needle 160 is disposed in the interior volume of the cowl 150. The first distal end of the shaft is connected to the hub. The shaft is configured to receive an implant 180. The cowl cap 152 is disposed partially within the hub. The implant 180 is secured in the shaft (e.g., prevented from falling out of the shaft) by the cowl cap 152 on one end of the shaft and the biocompatible tip 162 on a second end of the shaft.

In some embodiments, the implant injector device 100 is an Axitinib Intravitreal Implant injector and is a combination of two subcomponents of assemblies 110A-B. Assembly 110A may include an actuating device (e.g., plunger). Assembly 110B may contain a needle (e.g., 25G Injector) and/or the Intravitreal Implant. The implant injector device 100 may be packaged as two separate components to minimize the amount of material packaged with the implant (e.g., hydrogel implant), which reduce hydrogel degradation caused by the presence of moisture and reduce conditioning time (e.g., nitrogen conditioning, moisture removal). One or more components of assembly 110A may be made of acrylonitrile butadiene styrene (ABS). One or more components of assembly 110B may be made of polypropylene. One or more of the components of assembly 110B may be made of medical grade material (e.g., medical grade plastic).

The shaft (e.g., tube) of the needle 160 may be used for intravitreal injection by injecting the shaft of the needle 160 into the pars plana approximately 3.5-4 mm posterior to the limbus, with a slight downward (inferior) trajectory to the full penetration depth of the exposed portion of the shaft of the needle 160 (e.g., the portion of the shaft not covered by the cowl 150).

In some embodiments, the implant injector device 100 may use a two part injector design using an off-the shelf needle 160. In some embodiments, the needle 160 is custom-made for the implant injector device 100.

The cowl 150 (e.g., cowl halves 150A-B) has hook features that clip the assembly 110B securely onto the assembly 110A. Markings (e.g., alignment arrows) and a single operation assembly procedure contribute to ease of use.

The combination of design features associated with the wire 132 (e.g., rounded distal ends of the wire), body 120 (e.g., tapered or funneled interior surface of the body 120), and cowl 150 (e.g., tapered or funneled interior surface of the cowl 150) facilitate progression of the wire into the lumen of the shaft of the needle 160 to deploy the implant 180.

An axial force exerted on the distal end of the distal end of the plunger 130 in a syringe-like manner advances the wire 132 into the lumen of the shaft of the needle 160 to deploy the implant 180.

A living hinge on the body 120 creates friction agents on the plunger 130 to prevent unintentional movement of the plunger 130 prior to actuation of the plunger 130 (e.g., actuation via user input, the implant is to be deployed from the shaft responsive to the plunger clip being removed and the plunger being actuated by a first threshold force that is greater than a friction force of one or more living hinges of the body against the plunger). This also provides physical feedback during actuation which may be a standard for this type of procedure.

The plunger clip 140 is used to hold the plunger 130 locked in the loaded position. The plunger clip 140 snaps onto the body 120 (e.g., via a friction fit or a snap fit with curved surfaces of the plunger clip 140) and through slots on the plunger 130 to prevent movement until the plunger clip 140 is removed.

A protrusion on the plunger 130 interacts with the living hinge of the body 120 to prevent the plunger 130 from being removed from the body 120 (e.g., the plunger 130 includes a protrusion configured to actuate the living hinge of the body 120 responsive to the first threshold force, the protrusion prevents the plunger 130 from being removed from the body 120 responsive to actuation of the plunger 130 without a second threshold force).

In some embodiments, the wire 132 is glued onto the plunger 130, two body halves 120A-B are clipped together, an assembly of the wire 132 and plunger 130 glued together is slotted into the body 120 which funnels the wire 132 into the correct position. A needle 160 is sandwiched between two cowl halves 150A-B.

Migration of the implant 180 is mitigated by at least two factors: 1) a cowl cap 152 (e.g., plug, needle hub plug) is inserted into the hub of needle 160 to prevent proximal migration; and 2) a linear polyethylene glycol (PEG) (e.g., biocompatible tip 162) is deposited at the tip of the shaft (e.g., needle tip, tip of tube) to prevent distal migration.

The enclosures 190A-B may be foil packages. The assemblies 110A-B may be packaged in foil pouches for sterile and moisture barrier.

The cowl 150 may constrain injection depth to 4 millimeters (mm) to mitigate potential of the implant 180 contacting the retina during implantation, prior to hydration of the implant 180 (e.g., once hydrated the implant 180 becomes soft).

The biocompatible tip 162 (e.g., PEG tip) occludes the shaft of the needle 160 to prevent coring of thin ocular tissue. Foreign tissue matter left in the virous humor could elicit an immune response, infection, and/or could impact tolerability associated with drug product. Although embodiments of the present disclosure describe a biocompatible tip 162 on a distal end of a shaft of needle 160 of an implant injector device 100, in some embodiments, the biocompatible tip 162 can be used on a distal end of a shaft of a needle of other devices for similar or different applications. The biocompatible tip 162 (e.g., linear PEG) prevents ingress of vitriol fluid and pre hydration of the implant 180. The biocompatible tip 162 (e.g., PEG) may go into solution (e.g., dissolve, liquefy, etc.) when introduced to vitriol fluid to allow passage of the implant 180).

In some embodiments, the biocompatible tip 162 (e.g., PEG tip) is a linear 1 k PEG (1,000 molecular weight PEG) that is deposited at the tip of the shaft of the needle 160. The biocompatible tip 162 may prevent ingress of virtual fluid that could pre hydrate the implant, which could causes the implant 180 to swell and jam during actuation. The biocompatible tip 162 maybe 1 k PEG for quick dissolution, however other molecular weights may work as well. The biocompatible tip 162 may prevent coring of the ocular tissue which can remain in the vitreous and cause issues with tolerability and safety. The biocompatible tip 162 may prevent the implant 180 from falling out. In some embodiments, the biocompatible tip 162 (e.g., PEG tip) is an 8 k PEG (8,000 molecular weight PEG). In some embodiments, the biocompatible tip 162 (e.g., PEG tip) is about 1 k to about 8 k PEG (about 1,000 to about 8,000 molecular weight PEG).

Figure 1B:
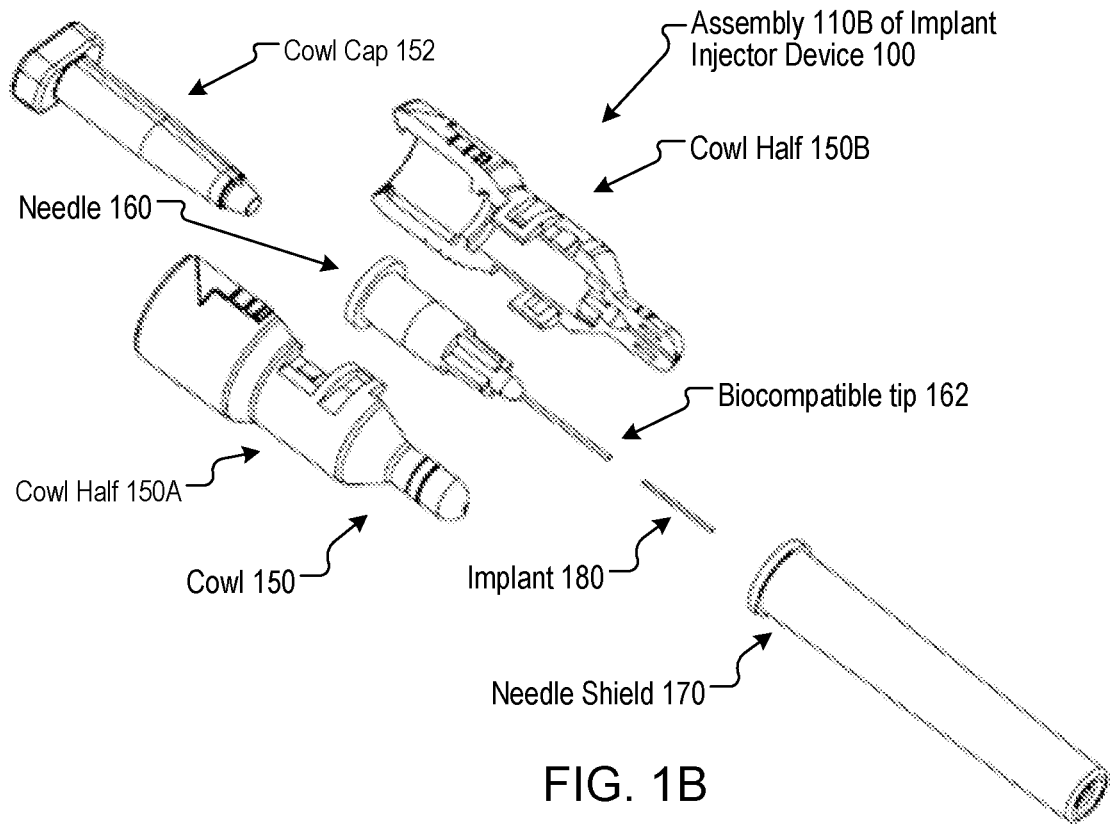
Figure 1E:
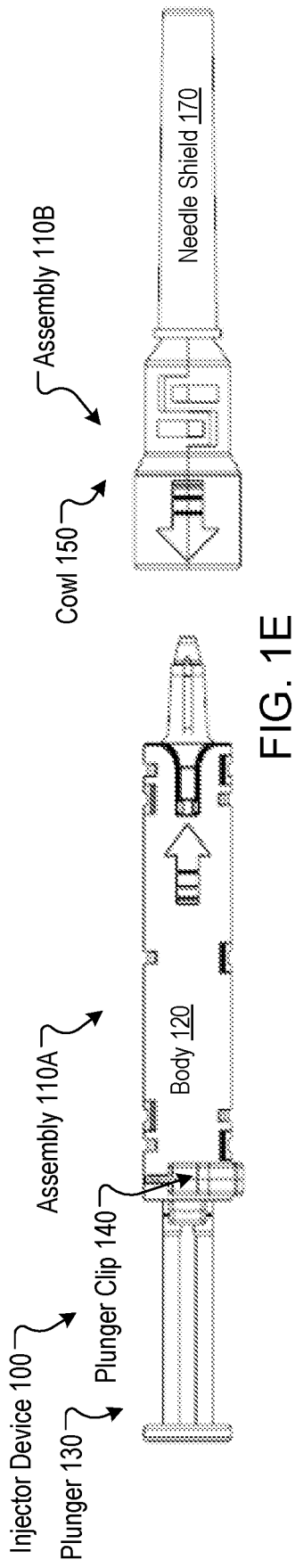

Referring to FIG. 1E, the assembly 110A is removed from enclosure 190A and assembly 110B is removed from enclosure 190B. The cowl cap 152 is removed from the assembly 110B. The assemblies 110A-B are aligned. In some embodiments, the assemblies 110A-B have markers (e.g., protrusions, markings, recesses, arrows, etc.) that indicate how the assemblies 110A-B are to be aligned. The assemblies 110A-B may be aligned when protrusions (e.g., of clips) of assembly 110B are aligned with recesses of assembly 110A.

Figure 1F:
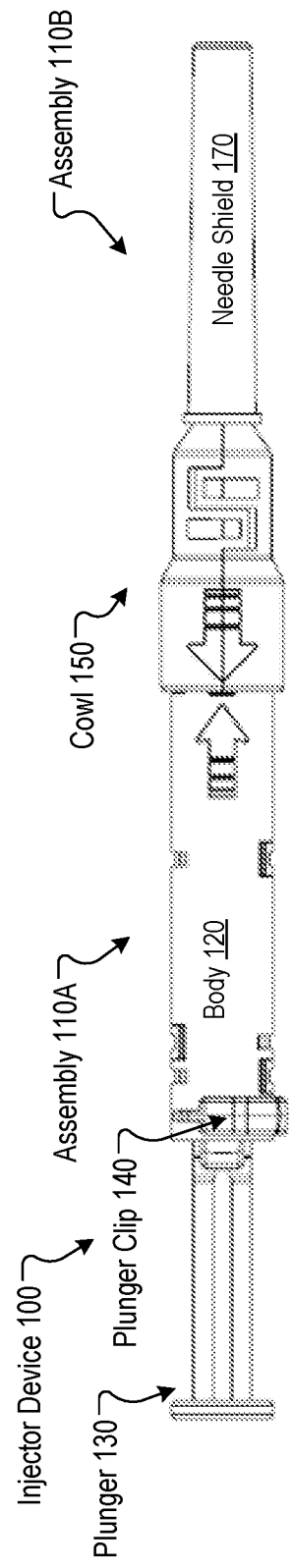

Referring to FIG. 1F, the assembly 110B is secured to the assembly 110A. In some embodiments, the interior protrusions (e.g., of clips) of cowl 150 are placed in exterior recesses of the body 120.

Referring to FIG. 1G, the plunger clip 140 is removed from the body 120 and plunger 130 and the needle shield 170 is removed from the cowl 150 to expose a portion of the shaft of needle 160.

Referring to FIG. 1H, the plunger 130 is actuated to push a wire 132 through the shaft of needle 160 to deploy the implant 180 from the needle 160. In some embodiments, a threshold force is used for a protrusion of the plunger 130 to pass a living hinge of the body 120 (e.g., the implant is to be deployed from the shaft responsive to the plunger clip being removed and the plunger being actuated by a first threshold force that is greater than a friction force of one or more living hinges of the body against the plunger). In some embodiments, responsive to the plunger 130 being actuated and the protrusions passing the living hinge of the body, the living hinge prevents the plunger 130 from being removed from the body 120 without a threshold force being used to pull the protrusions of the plunger 130 through the living hinge.

Figure 2A:
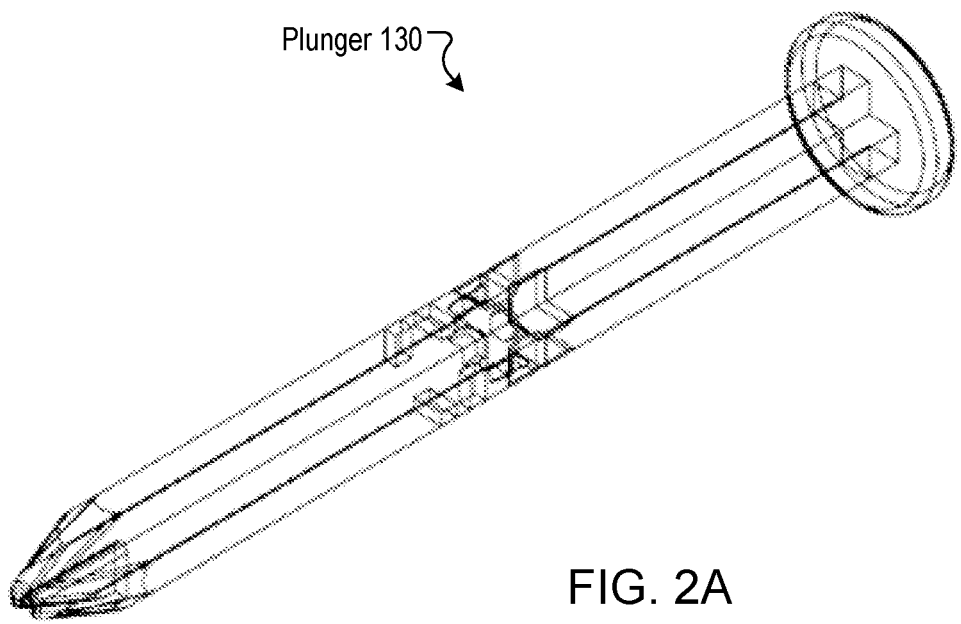
FIGS. 2A-E illustrate a plunger of an implant injector device, according to certain embodiments.
Figure 2B:
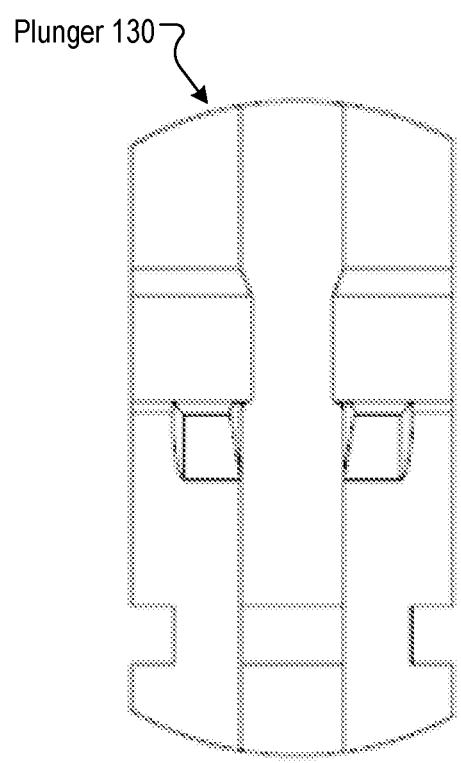
Figure 2C:
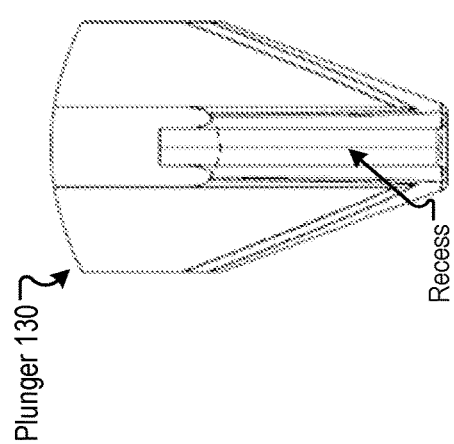
Figure 2D:
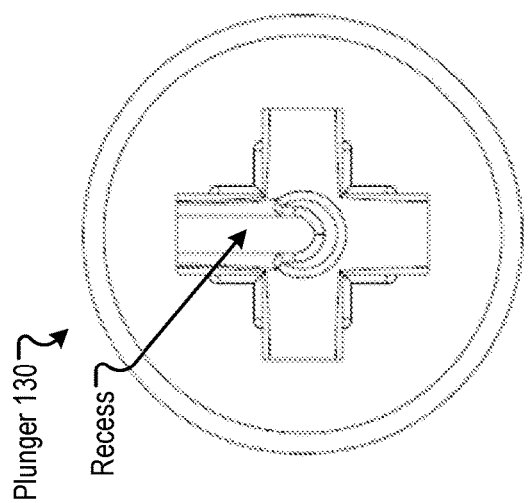
Figure 2E:
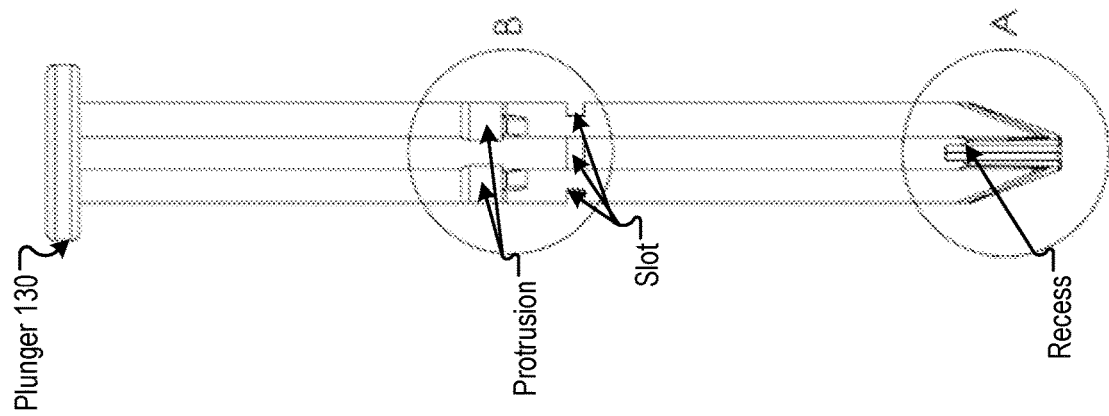

FIGS. 2A-E illustrate views of a plunger 130 of an implant injector device 100, according to certain embodiments. FIG. 2A may illustrate a perspective view of the plunger 130, FIG. 2B may illustrate a side view of a middle portion of the plunger 130, FIG. 2C may illustrate a side view of a distal end of the plunger 130, FIG. 2D may illustrate a front view of a distal end of the plunger 130, and FIG. 2E may illustrate a side view of the plunger 130.

The plunger 130 is used to transmit an axial force in a syringe-like manner to deploy the implant 180 (e.g., insert) into the vitreous. The plunger 130 has a slot on the distal end for gluing the wire 132 (e.g., nitinol wire) (e.g., see FIG. 2C).

The plunger 130 has a cutout slot (e.g., see FIG. 2C, about 4 to 5 mm wide) that interfaces with the plunger clip 140 to hold the assembly of the plunger 130 and wire 132 in the locked position prior to use.

The plunger 130 may have a cross-shaped profile that interfaces with the living hinge (e.g., friction arms) of the body 120 to prevent unintentional movement and to provide a little resistance when actuated. Plunger 130 may be symmetrical so that the plunger can be rotated 90 degrees and still be insertable in the body 120.

The plunger 130 in the locked position may have a recess that does not interface with the living hinge (e.g., friction arms) so that the arms do not plastically deform over time. The plunger may have a protrusion adjacent to the recess that constrains the plunger from 130 being easily removed from the body 120.

The wire 132 may be a nitinol wire. The wire 132 may be about 0.30-0.35 mm×41-42 mm. The wire 32 may be used to deploy implant 180 by transmitting an axial force from the plunger 130. The wire 132 may be rounded on both distal ends to facilitate entry into the needle 160 and to prevent particulate generation when the wire 132 travels through the shaft of the needle 160 (e.g., the stainless steel shaft of the needle 160). The wire 132 may be flexible and may have a shape memory material properties for assembling to avoid kinking (e.g., easily and/or permanently kinking) during assembly. Wire 132 made of nitrinol may maintain an original shape after assembly (e.g., not kinking).

Figure 3B:
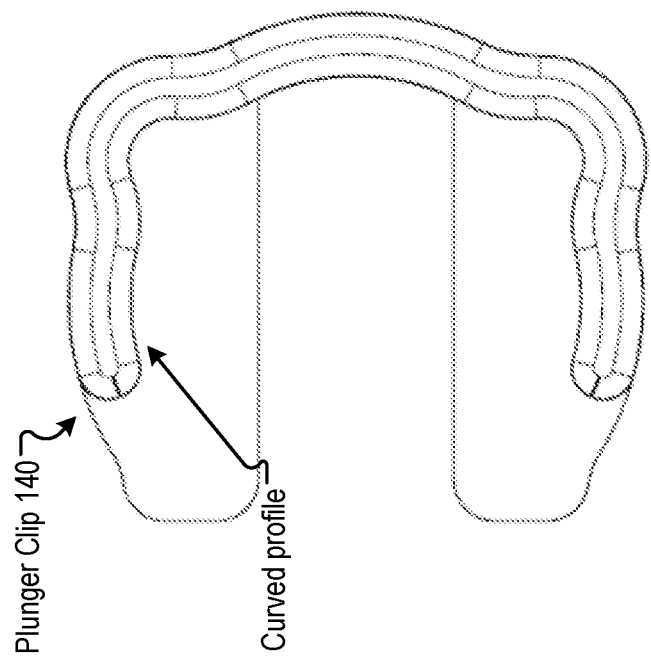
FIGS. 3A-C illustrate a plunger clip of an implant injector device, according to certain embodiments.
Figure 3A:
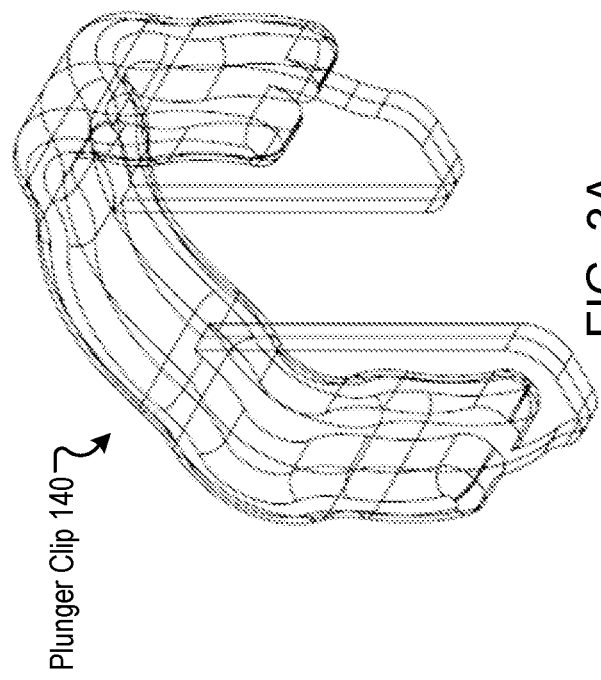
Figure 3C:
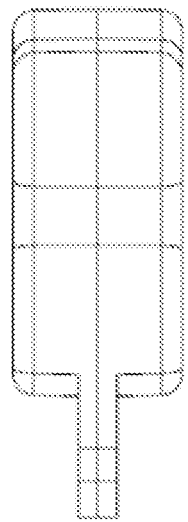

FIGS. 3A-C illustrate a plunger clip 140 of an implant injector device 100, according to certain embodiments. FIG. 3A may illustrate a perspective view of the plunger clip 140, FIG. 3B may illustrate an upper view of the plunger clip 140, and FIG. 3C may illustrate a side view of the plunger clip 140.

Plunger clip 140 may lock the plunger 130 into the loaded position. The flanges of the plunger clip 140 may pass through slots on the body 120 and interface with the cutout slots on the plunger 130. The plunger clip 140 may have a circular profile (e.g., curved profile) to physically clip onto the circular body 120. The plunger clip 140 may be rounded to mitigate perforation of the enclosure 190 (e.g., pouch).

Figure 4B:
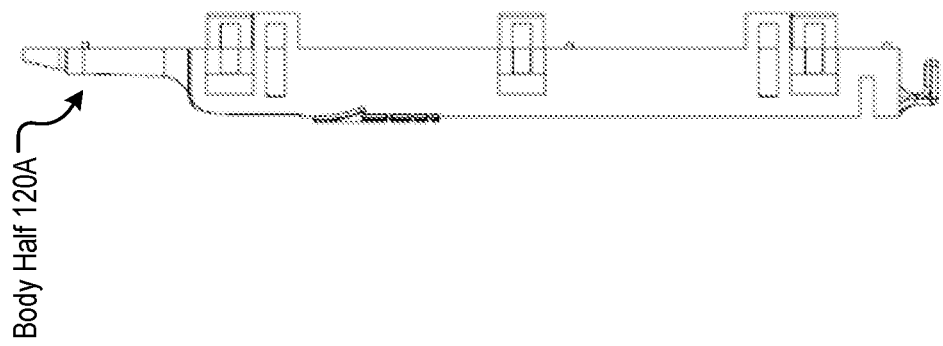
FIGS. 4A-D illustrate a body half of an implant injector device, according to certain embodiments.
Figure 4A:
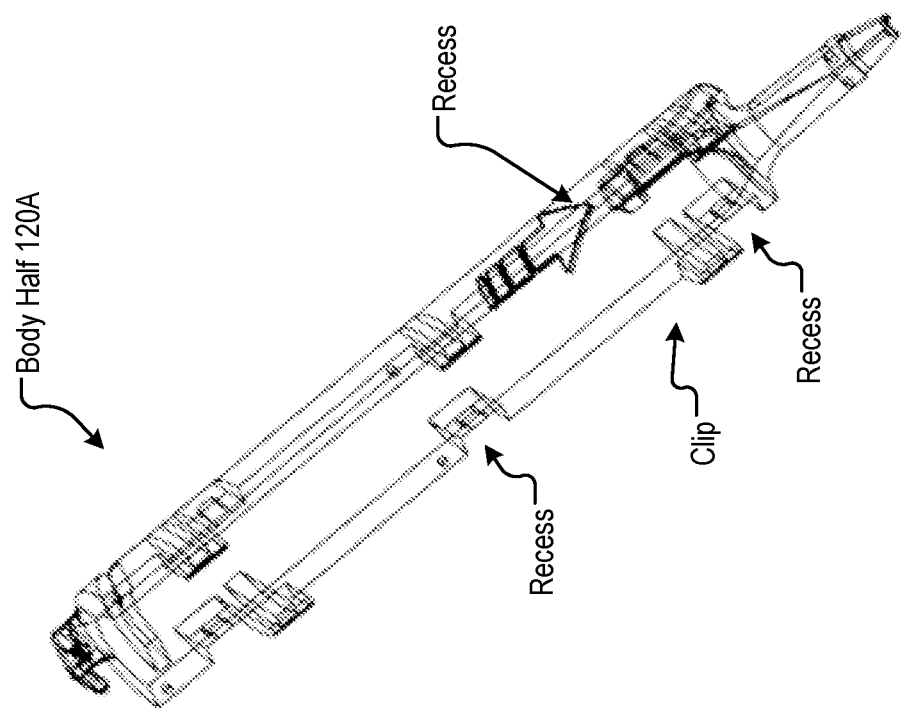
Figure 4C:
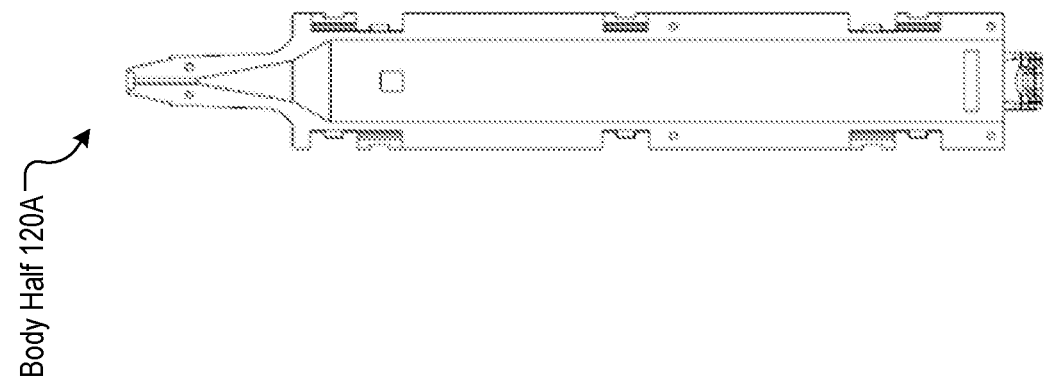
Figure 4D:
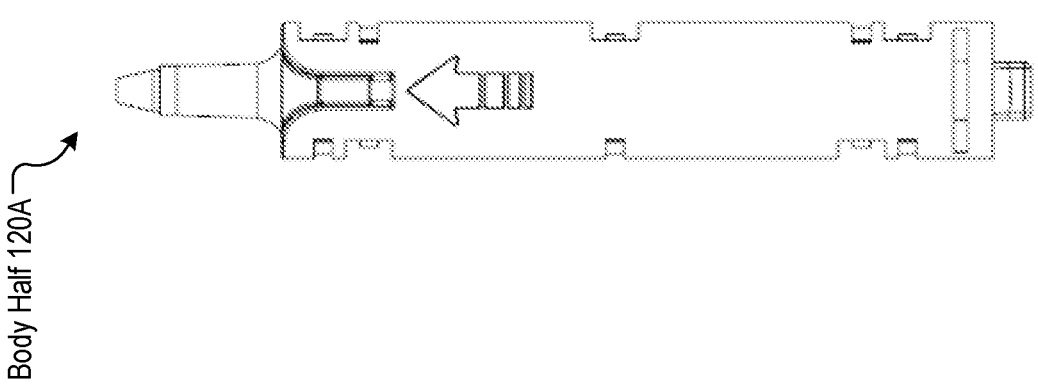

FIGS. 4A-D illustrate a body half 120A of an implant injector device 100, according to certain embodiments. FIG. 4A may illustrate a perspective view of the body half 120A, FIG. 4B may illustrate a side view of the body half 120A, FIG. 4C may illustrate a front view of the body half 120A, and FIG. 4D may illustrate a rear view of the body half 120A.

The body 120 may be two body halves 120A-B that clip together for easier manufacturability (e.g., injection molding). The female and male clip features are positioned to the left and right sides of the body 120 in an alternating pattern to keep the two body halves 120A-B secured and aligned when snapped together. The position of the clips constrains the two body halves 120A-B from sliding in the lateral direction.

The mirrored patterned of female and male clip features is oriented so that only one design is used. The body half 120A and 120B can clip onto itself when rotated 180 degrees.

A male and female alignment pin counterpart are positioned in locations (e.g., three locations) along the seam of the body to further prevent lateral movement and to avoid misalignment.

The geometry of the tip of the body is designed to match (e.g., perfectly match) the inner dimensions of a hub of needle 160 (e.g., JBP needle hub) to maintain alignment. Geometry is slightly oversized to create a friction fit that pinches the body halves 120A-B together which also aids alignment.

The internal funnel features of the body 120 aids assembly when the assembly of the plunger 130 and wire 132 is slotted into the body 120. The funnel guides the wire into the wire channel of the body 120. The wire channel constrains the wire 132 and keeps the wire 132 from buckling. The wire channel guides the wire 132 into the lumen of the shaft of the needle 160.

The living hinge (e.g., friction arms, about 0.8 to 0.9 mm) of the body 120 in the resting state are separated by a distance that is less than the width of the plunger 130. This may result in a medial force against the plunger 130, which translates a friction force that prevents the plunger 130 from moving in the axial direction until a threshold force is applied (e.g., about 1-3 Newtons, the force for plunger actuation for surgical instruments).

A female snap feature of the body 120 may interface with the cowl 150 to securely connect the needle 160 to the assembly 110A. This may provide for ease of assembly.

Figure 5A:
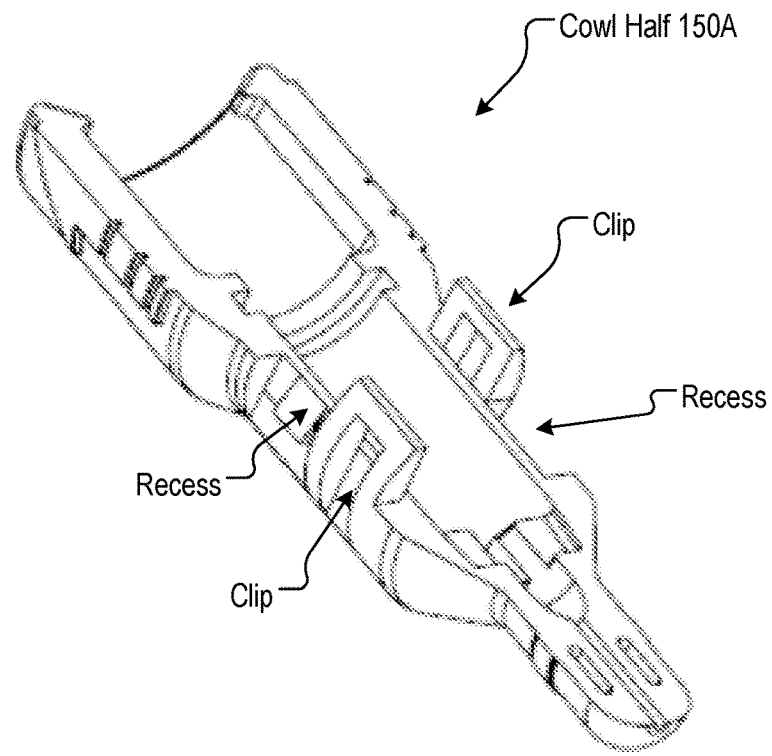
FIGS. 5A-E illustrate a cowl half of an implant injector device, according to certain embodiments.

FIGS. 5A-E illustrate a cowl half 150A of an implant injector device 100, according to certain embodiments. FIG. 5A may illustrate a perspective view of the cowl half 150A, FIG. 5B may illustrate a side view of the cowl half 150A, FIG. 5C may illustrate a front view of the cowl half 150A, FIG. 5D may illustrate a rear view of the cowl half 150A, and FIG. 5E may illustrate an upper view of the cowl half 150A.

The cowl 150 may include two hooks on left and right inner seam of the cowl halves 150A-B to clip onto the body 120. The slots of the body 120 that receives the hooks of the cowl 150 may also press the hooks from one cowl half 150A against the other cowl half 150B, clamping the cowl halves 150A-B together. This in combination with the male and female clips hold the cowl halves 150A-B together and prevents lateral deflection of the assembly 110B.

The proximal end of the cowl 150 (e.g., hook side) sheaths over the outer diameter of the body 120. This prevents lateral deflection of the assembly 110B and maintains concentricity.

The cowl 150 covers a portion of the needle 160 (e.g., 13 mm needle) to constrain the injection depth to about 4 mm. This is used for intravitreal deposition of a rigid polymer implant to avoid potential contact of the retina. An eyeball may be about 22 mm in diameter, about 4 mm injection depth plus about 16.7 mm implant 180 (e.g., 200 ug formulation) is about 21.7 mm. An implant 180 of 600 ug may be about 8 mm.

Annular protrusion (e.g., needle end) of the cowl 150 may interface with a needle shield 170 (e.g., JBP needle cap) to hold the needle shield 170 in place. The cowl 150 may be configured to hold a JPB 13 mm×25 G needle.

Figure 5B:
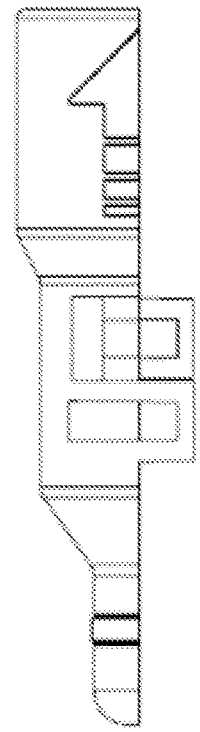
Figure 5E:
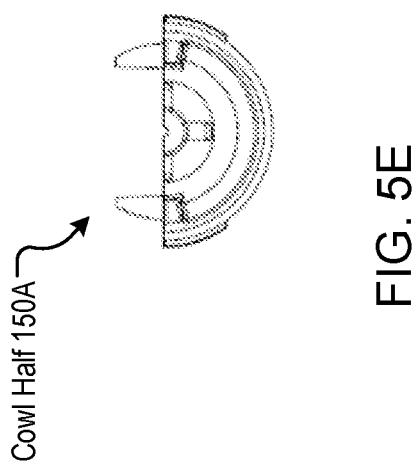
Figure 5D:
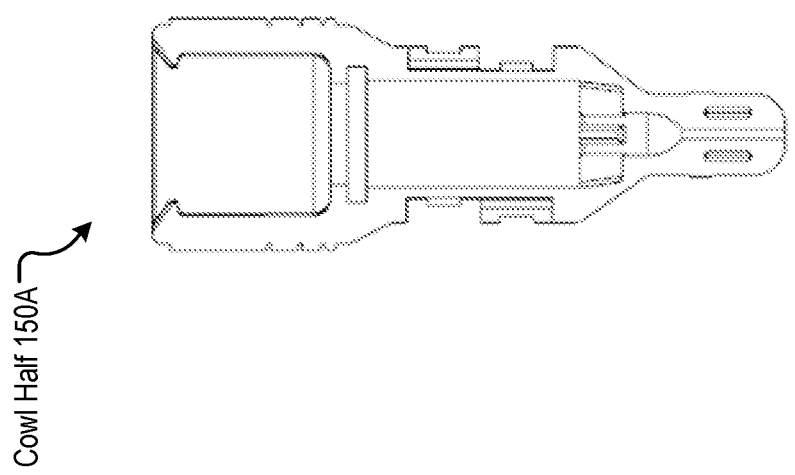
Figure 5C:
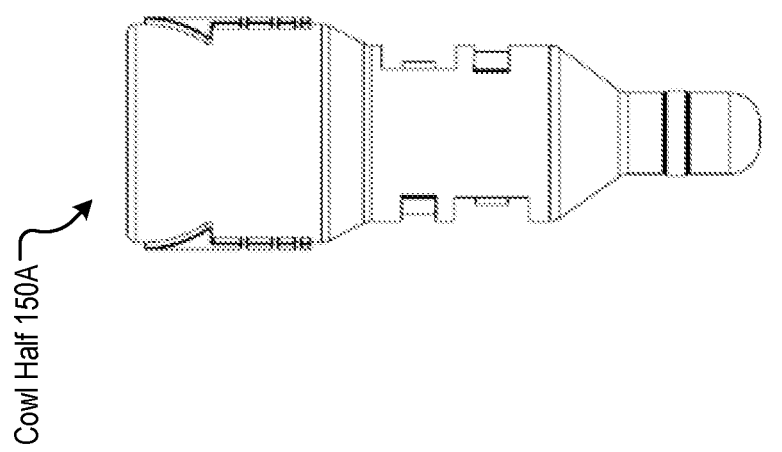

FIG. 6A-B illustrate a cowl cap 152 (e.g., plug, needle hub plug) of an implant injector device 100, according to certain embodiments FIG. 6A may illustrate a perspective view of the cowl cap 152 and FIG. 5B may illustrate a side view of the cowl cap 152.

The cowl cap 152 may be inserted into the back end of the hub of needle 160 and held in place via friction fit to retain the implant 180 during shipping and handling. The cowl cap 152 may include one or more recesses along the sidewalls of the cowl cap 152 to allow for moisture removal (e.g., nitrogen conditioning) within the shaft of the needle 160 (e.g., conditioning of the implant 180).

Figure 7:
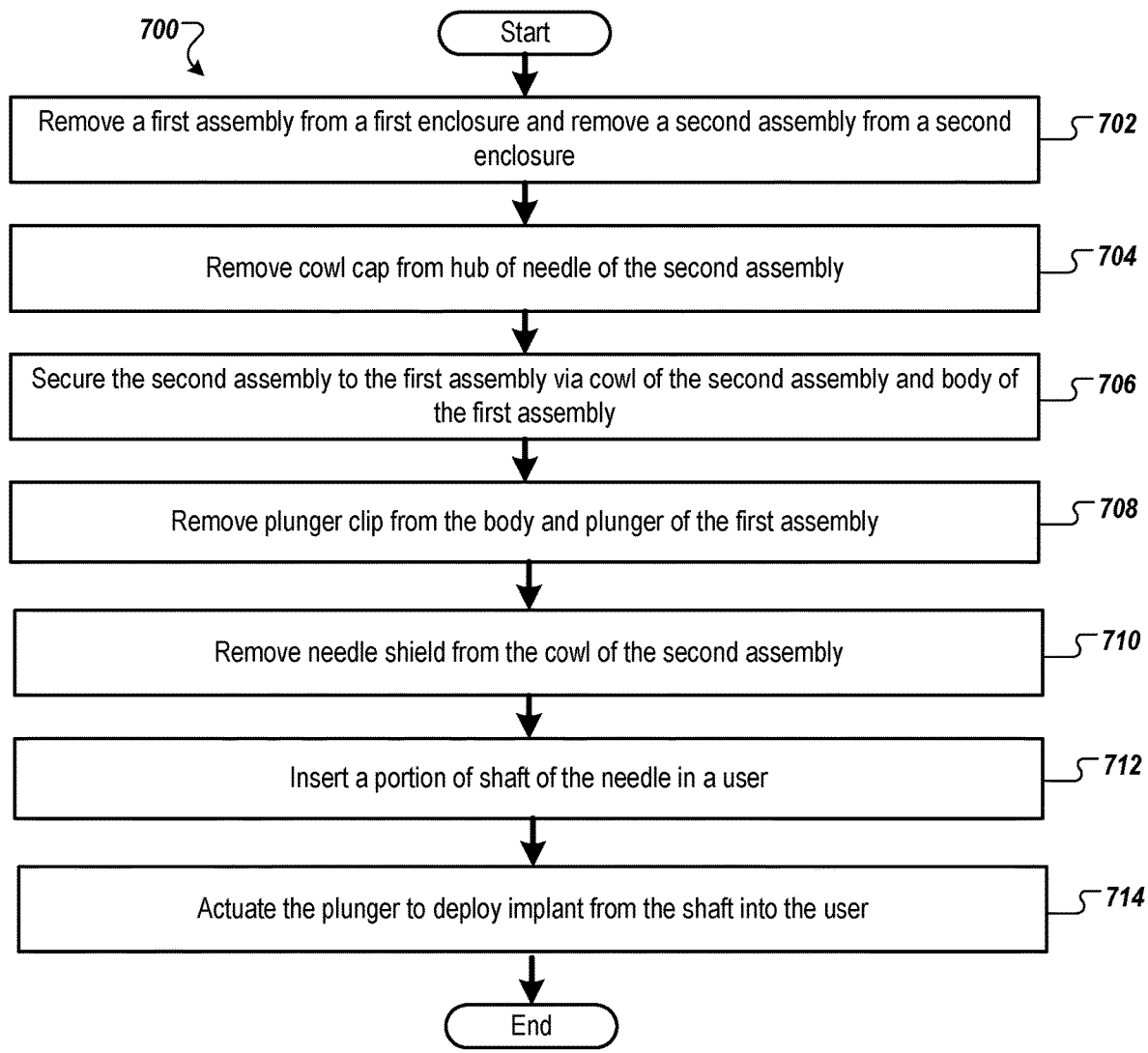
FIG. 7 illustrates a method of treatment of administering an implant using an injector device, according to certain embodiments.

FIG. 7 illustrates a method 700 of treatment of administering an implant (e.g., implant 180) using an implant injector device (e.g., implant injector device 100), according to certain embodiments. Although shown in a particular sequence or order, unless otherwise specified, the order of the operations can be modified. Thus, the illustrated embodiments should be understood only as examples, and the illustrated operations can be performed in a different order, and some operations can be performed in parallel. Additionally, one or more operations can be omitted in various embodiments. Thus, not all operations are required in every embodiment.

At block 702, a first assembly is removed from a first enclosure and a second assembly is removed from a second enclosure At block 704, a cowl cap (e.g., plug, needle hub plug) is removed from a hub of a needle of the second assembly.

At block 706, the second assembly is secured to the first assembly via a cowl of the second assembly and a body of the first assembly. In some embodiments interior protrusions (e.g., of clips) of the cowl interface with exterior recesses of the body.

At block 708, a plunger clip is removed from the body and the plunger of the first assembly. The plunger clip may be secured to the body via a friction fit or a snap fit and a threshold force may be used to remove the plunger clip from the body and plunger.

At block 710, the needle shield is removed from the cowl of the second assembly.

At block 712, a portion of the shaft of the needle is inserted in a user. The portion of the shaft may be the length of the shaft that is not covered by the cowl. The portion of the shaft may be in the user for a threshold amount of time (e.g., about 1 to about 5 seconds) to at least partially dissolve a biocompatible (e.g., PEG, polymer) tip on the shaft (e.g., on the bevel of the shaft) to allow the implant to pass through the shaft.

At block 714, the plunger is actuated to deploy the implant from the shaft into the user. A threshold force may be used to actuate the protrusion of the plunger past the living hinge of the body (e.g., the implant is to be deployed from the shaft responsive to the plunger clip being removed and the plunger being actuated by a first threshold force that is greater than a friction force of one or more living hinges of the body against the plunger). Responsive to the protrusion of the plunger being actuated past the living hinge of the body, the living hinge of the body may prevent the protrusion of the plunger from returning to the original location without a threshold force.

Figure 8:
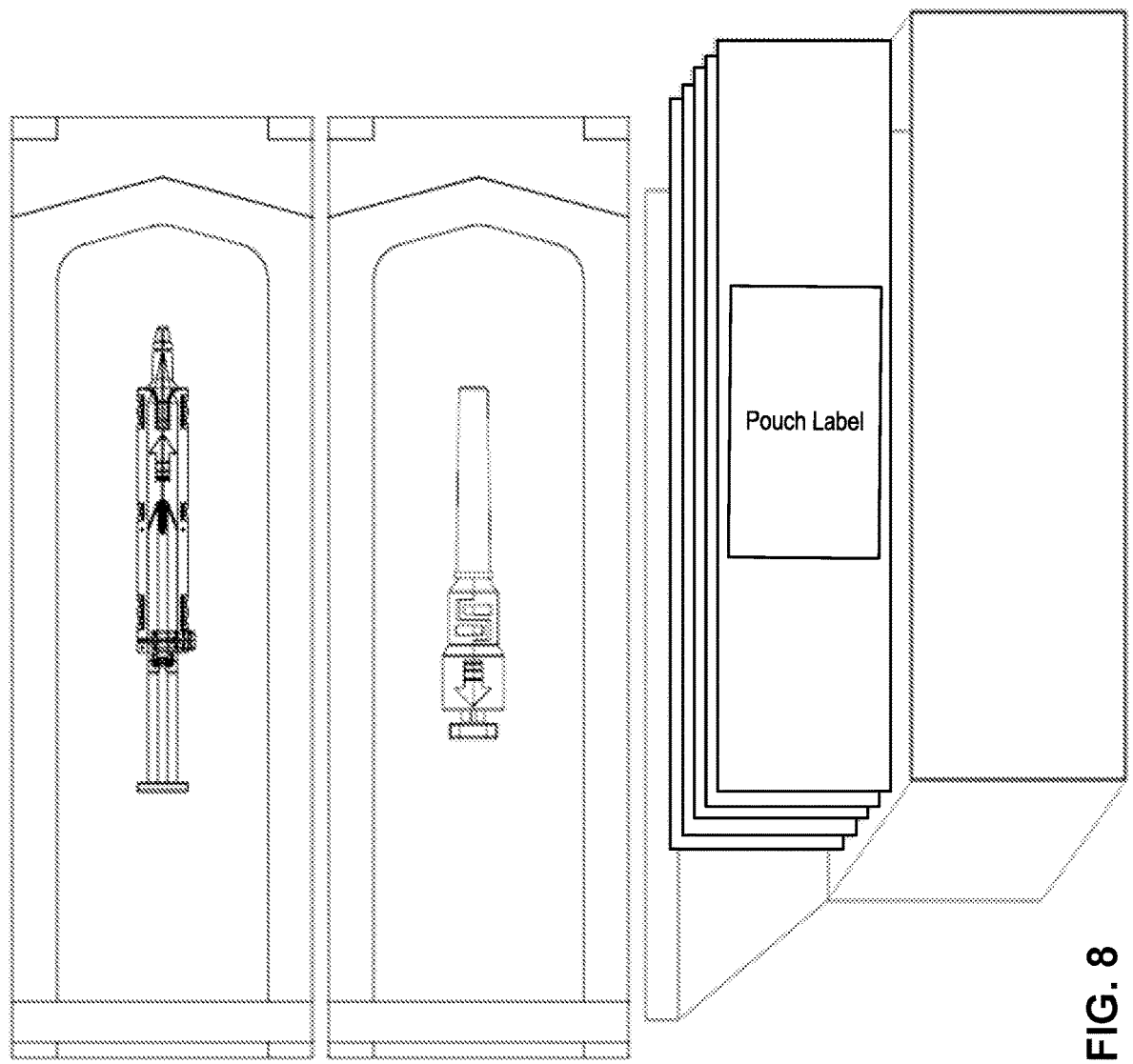
FIG. 8 is a schematic representation of implant injector device packaging, according to certain embodiments.

FIG. 8 is a schematic representation of implant injector device packaging, according to certain embodiments. One or more of the features (e.g., structure, functionality, etc.) of implant injector devices described herein may be used with the implant injector devices of FIG. 8.

In this embodiment, implants are pre-loaded into thin-walled needles separately packaged from the injection device. An all-in-one device with needles already connected to the injection device is also possible.

In certain embodiments, an injection device, such as a syringe or another injection device, may be separately packaged and sterilized e.g. via gamma irradiation.

In certain embodiments, a kit (which may also be referred to as a "system") includes one or more sustained release biodegradable ocular implant(s) or manufactured in accordance and one or more needle(s) for injection, wherein the one or more needle(s) is/are each pre-loaded with one sustained release biodegradable ocular implant in a dried state. In certain embodiments the needle(s) is/are 25- or 27-gauge needle(s) or may be smaller gauge, such as 30-gauge needle(s). The diameter of the needle is chosen based on the final diameter of the implant in the dried (and optionally stretched) state. The active contained in the implant is generally a TKI, such as axitinib.

In one embodiment the kit comprises one or more, such as two or three 25- or 27-gauge needle(s) each loaded with an implant containing axitinib in an amount in the range from about 180 µg to about 220 µg, or in an amount of about 200 µg.

In yet another embodiment the kit comprises one 25-gauge needle loaded with an implant containing axitinib in an amount in the range from about 540 µg to about 660 µg, or in an amount of about 600 µg. In another embodiment, the kit comprises one 27-gauge needle loaded with an implant containing axitinib in an amount in the range from about 540 µg to about 660 µg, or in an amount of about 600 µg.

If two or more implants are contained in the kit, these implants may be identical or different, and may contain identical or different doses of TKI.

In certain embodiments, the lumen of the needle containing the implant may be occluded by a material that is solid at room temperature but soft or liquid at body temperature, such as a 1 k PEG material.

The kit may further contain an injection device for injecting the implant(s) into the eye of a patient, such as into the vitreous humor of the patient. In certain embodiments the injection device is provided and/or packaged separately from the one or more needle(s) loaded with implant. In such embodiments the injection device may be connected to the one or more needle(s) loaded with implant prior to injection.

In certain embodiments the number of injection devices provided separately in the kit equals the number of needles loaded with the implant provided in the kit. In these embodiments the injection devices are only used once for injection of one implant.

In other embodiments the kit contains one or more injection device(s) for injecting the implant into the eye of a patient, such as into the vitreous humor of the patient, wherein each injection device is or is not pre-connected to a needle loaded with implant. A pharmaceutical product may include a sustained release biodegradable ocular implant loaded in a needle and an injection device, wherein the needle is pre-connected to the injection device. In case the needle is not yet pre-connected to the injection device, the physician administering the implant is to remove both the needle containing the implant and the injection device from the packaging, and connect the needle to the injection device to be able to inject the implant into the patient's eye.

In some embodiments the injection device contains a push wire to deploy the implant from the needle into the vitreous humor. The push wire may be a Nitinol push wire or may be a stainless steel/Teflon push wire. The push wire allows deploying the implant from the needle more easily.

In other embodiments the injection device and/or the injection needle may contain a stop feature that controls the injection depth.

In some embodiments the injection device is or comprises a modified Hamilton glass syringe that may be placed into a plastic syringe housing, such as inside an injection molded housing. A push wire, such as a Nitinol wire, is inserted into the syringe and advances with the plunger of the syringe during deployment of the implant. To facilitate entry of the nitinol push wire into the needle, a hub insert may be added into the needle hub.

Figure 9A:
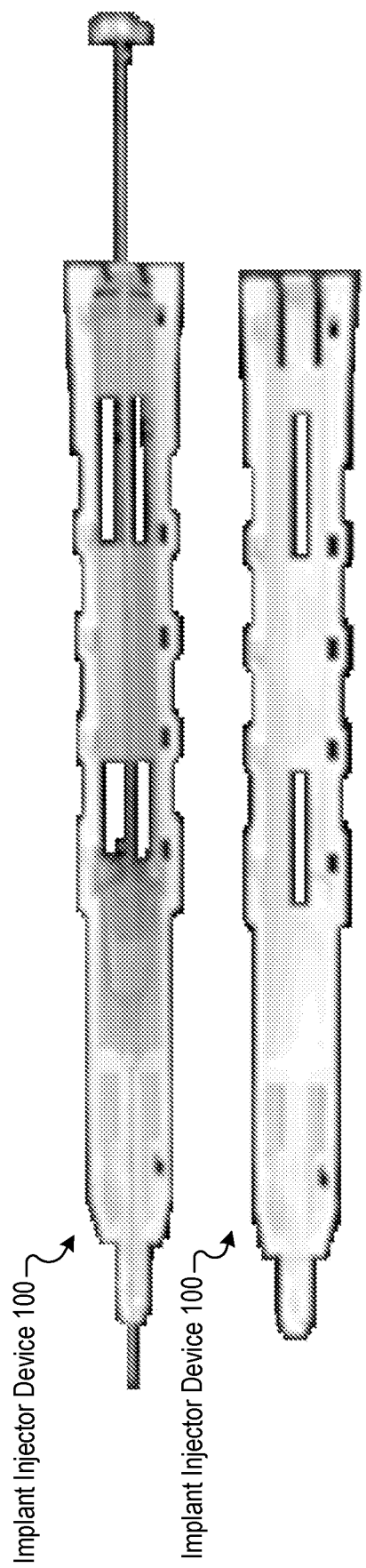
FIGS. 9A-B illustrate implant injector devices, according to certain embodiments.
Figure 9B:
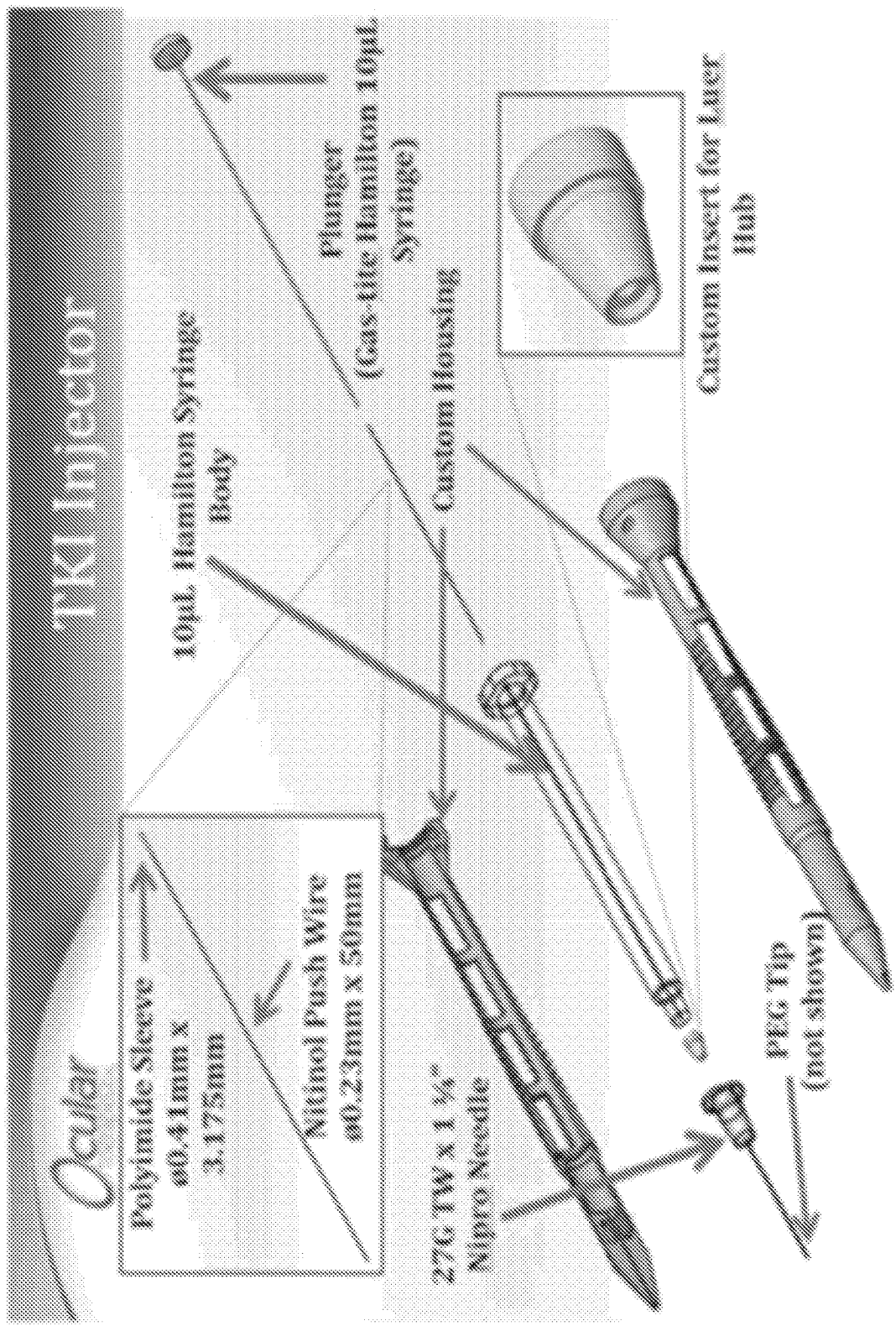

FIGS. 9A-B illustrate implant injector devices 100 (e.g., for injecting an implant into the vitreous humor of a patient), according to certain embodiments. One or more of the features (e.g., structure, functionality, etc.) of implant injector devices described herein may be used with the implant injector devices 100 of FIGS. 9A-B.

This depicted embodiment of an injector may include a Hamilton syringe body and/or a Nitinol push wire to deploy the implant. FIG. 9A shows the body (e.g., Hamilton syringe body) inside of an injection molded casing. FIG. 9B shows a schematic view of the components of this embodiment of the injector. In certain embodiments, the injector comprising the body (e.g., Hamilton syringe body) and the plastic housing parts are pre-assembled in a kit and the injector is ready for use (without or without mounted needle containing the implant). In other embodiments, the injector may be assembled by the physician prior to mounting the needle containing the implant.

In other embodiments, the injection device is an injection molded injector. A schematic exploded view of an embodiment of such injection molded injector is shown in FIGS. 1A-B. In this case the number of assembly steps by the physician just prior to administering the implant to a patient is reduced.

The kit may further comprise one or more doses, in particular one dose, of an anti-VEGF agent ready for injection. The anti-VEGF agent may be selected from the group consisting of aflibercept, bevacizumab, pegaptanib, ranibizumab, and brolucizumab. In certain embodiments the anti-VEGF agent is bevacizumab. In other embodiments the anti-VEGF agent is aflibercept. The anti-VEGF agent may be provided in a separate injection device connected to a needle, or may be provided as a solution or suspension in a sealed vial, from which the solution or suspension may be aspirated through a needle into a syringe or other injection device prior to administration.

The kit may further comprise an operation manual for the physician who is injecting the ocular implant(s). The kit may further comprise a package insert with product-related information.

In addition to the kit, an injection device per se that is suitable for injecting a sustained release biodegradable ocular implant into the eye. The injection device may connect the injection device to a needle, wherein the needle is pre-loaded with the implant. The injection device may further contain a push wire to deploy the implant from the needle into the eye when the injection device has been connected to the needle, which push wire may be made of Nitinol or stainless steel/Teflon or another suitable material. The injection device may further be obtainable by affixing the wire to the plunger and encasing it between two snap fit injector body parts and securing the plunger with a clip. An injection device and a needle pre-loaded with implant in accordance with certain embodiments of the present disclosure is depicted in FIG. 8.

In certain embodiments, the implant may be administered via an injection device according to the present disclosure connected to a needle pre-loaded with implant as disclosed herein, or may be administered via another injection device suitable to be connected to a needle pre-loaded with an implant as disclosed herein, such as a (modified) Hamilton syringe. In other embodiments, a hollow microneedle may be used for suprachoroidal administration as disclosed in U.S. Pat. No. 8,808,225 which is incorporated by reference herein.

In embodiments wherein two or more implants are administered, the implants are generally administered concurrently as disclosed herein above. The implants administered concurrently can be the same or different. In cases where an administration during the same session is not possible e.g. due to administration complications or patient-related reasons a successive administration during two or more different sessions may alternatively be applied, such as for instance administration of two implants 7 days apart. This may still be considered as a "concurrent" administration in the context of the present disclosure.

In certain embodiments the dry implants are loaded in a needle, such as a 25-gauge or a 27-gauge needle, or a smaller gauge needle, for injection and are administered to the eye, e.g. to the vitreous humor, through this needle. In one embodiment, the injector used for injecting the implant into the eye is an injection device according to another aspect of the present disclosure as disclosed above. Implants containing 200 µg and 600 µg, respectively, that are suitable for the therapeutic applications.

In some embodiments, a pharmaceutical product comprising the sustained release biodegradable ocular implant loaded in a needle and an injection device, wherein the needle is pre-connected to the injection device.

In some embodiments, loaded needles (e.g., implant injector device 100 and/or assembly 110B) may be placed into a glove box for 6 to 9 days to remove any moisture (the remaining water content in the implant is intended to not exceed 1% water). All operations from then on may be performed in the glove box. The loaded needle may be dipped into a melted low-molecular weight 1 k PEG to tip the needle. Upon cooling a hardened small drop of PEG remains, which provides lubricity, keeps the implant in place within the needle, allows successful deployment and prevents premature rehydration of the implant within the needle during administration. Moreover, PEG tipping is minimizing tissue injury i.e. tissue coring, a process by which pieces of tissue are removed by a needle as it passes through the tissue. The PEG-tipped needles may then be again inspected, needles which did not meet the quality requirements may be discarded. Passed needles may be again capped to ensure the needles are not suffering any additional damage. Needles may then be individually pouched and sealed to prevent them from moisture and keep them sterile. The injection device, for instance a modified Hamilton glass syringe, had a push wire (e.g. a Nitinol push wire) that allows deploying the implant from the needle more easily. The injection needle may contain a stop feature that controls the injection depth. The injection device can be separately packaged and sealed under nitrogen in foil pouches in the same way as described for the needle (FIG. 8), or could be pre-assembled with the implant-loaded needle or within a preloaded injector. The packaged needles and injection devices may be removed from the glove box and stored refrigerated (2-8° C.) prior to sterilization using gamma irradiation. After sterilization the packages may be stored refrigerated (2-8° C.) or frozen protected from light prior to use and may be equilibrated 30 min to room temperature prior to injection.

Figure 10A:
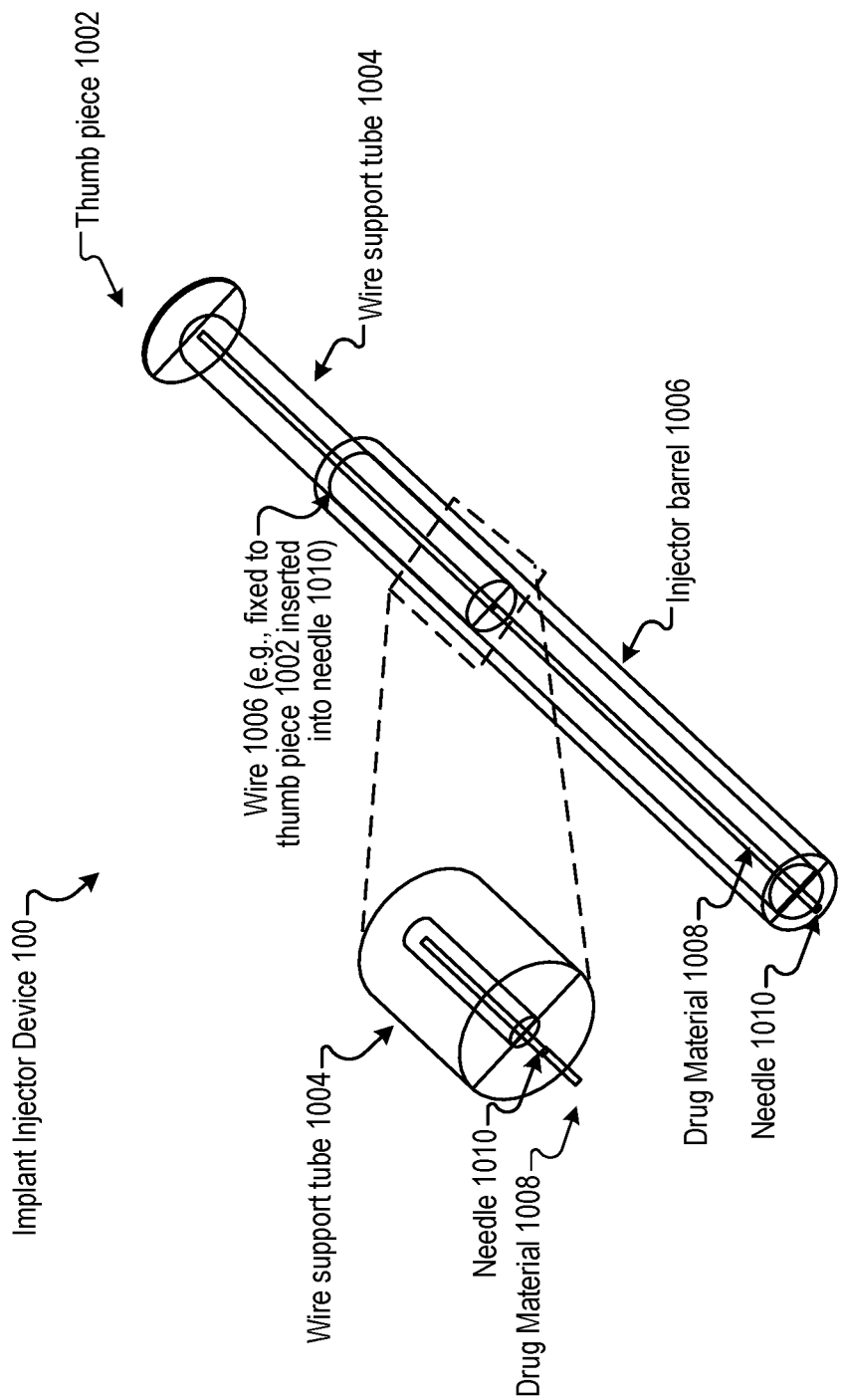

FIGS. 10A-C illustrate implant injector devices 100, according to certain embodiments. One or more of the features (e.g., structure, functionality, etc.) of implant injector devices 100 described herein may be used with the implant injector devices 100 of FIGS. 10A-C. In some embodiments, the implant injector devices 100 are a tube-in-a-tube-in-a-tube injector (e.g., or a tube-in-a-tube-in-a-tube-in-a-tube injector) that feeds a nitinol wire through a needle lumen which pushes a fiber of drug material (e.g., implant 180) out of the needle).

In some embodiments, the implant injector device 100 of one or more of FIGS. includes one or more of a thumb piece 1002, a wire support tube 1004, a wire 1006 (e.g., fixed to the thumb piece inserted into needle), an injector barrel 1006, a drug material 1008, and/or a needle 1010.

In many anatomical locations, very fine needle sizes are used for injection. Implants for sustained drug delivery can be injected using syringe-like devices where the implant is housed within the needle lumen and ejected using a push-rod after tissue penetration. These implants may have specific size requirements so they can hold an adequate dose of drug, and possibly other excipients. Fine needles, with very narrow internal diameter, may require elongation of the implant to achieve adequate overall dimensions or mass to contain the drug dose, thus may use long push-rods or wires to eject the implant. Unsupported wires with high slenderness ratios may easily buckle under axial loading, thus rendering the wire unable to transmit the ejection force to the implant.

In some embodiments, a syringe-like device (e.g., implant injector device 100) uses concentric shapes, such as tubes, that can the used in a syringe-like manner to transmit an axial load to eject the implant while providing support to the push-wire. An implant injector device is depicted in FIGS. 10A-C and may be depicted in other FIGS. herein (e.g., FIGS. 1A-H). The wire uses support to minimize buckling and lateral deflection. The basic design called "tube in a tube in a tube" uses an elongated needle that extends into the device body (tube 1), which contains the implant within its lumen. Also, within the needle lumen is a short length of the push-wire, which snugly fits within the ID of the needle lumen. This short length directs the push-wire into the needle at the initiation of the injection stroke. The bulk of the push-wire is contained within the lumen of a second tube (plunger) that snugly fits around the needle outside diameter, with a short portion of the push-wire inserted into the needle lumen. Finally, the outer body of the device has internal dimensions that snugly fit around the outer diameter of the plunger, giving the user a way to hold the device while pushing the plunger. When the plunger is pushed, the wire is forced into the needle—the inside wall of the plunger preventing excessive deflection of the wire, maintaining the axial force vector direction into the needle and towards the implant.

For extremely fine needles, a fourth tube can be used to prevent deflection of the needle during implant deployment. This design is referred to as "tube in a tube in a tube in a tube." The fourth tube, or "needle sleeve," is simply a sleeve snugly fitting around the needle. The plunger ID is then enlarged enough to snugly fit around the OD of the needle sleeve. The needle sleeve wall thickness and correspondingly larger lumen of the plunger may be sized to provide adequate support to the wire.

The force to eject implants under physiological conditions may provide a power law function of transmitted force to wire slenderness ratio. The slenderness ratio is the length of wire from the end of the needle to the end of the plunger lumen prior to initiation of the injection stroke. The force to move the implant within the needle lumen ($F_f$) is to be exceeded by the force transmitted through the push-wire ($F_m$), i.e. $F_m/F_f$ is to be greater than 1 or the device may fail. Solving the best fit power law function for $F_m/F_f=1$ provides the maximum allowable slenderness ratio capable of transmitting the force for implant ejection. Multiplying the maximum slenderness ratio by the wire radius gives the maximum length of wire within the lumen of the plunger. The ability to transmit force was found to be proportionate to the wire modulus, which is material specific.

The wire OD may be snugly matched to the ID of the needle. A snug fit prevents lateral deflection and buckling within the needle lumen. A snug fit also prevents lateral overlap of the push-wire and the implant within the needle lumen during deployment.

The implant diameter may be snugly matched to the wire ID. A snug fit minimizes potential for deflection and buckling of the implant during deployment. In addition, a snug fit prevents lateral overlap of the push-wire within the needle lumen during deployment. The implant may not be longer than the maximum length of the push wire spanning the plunger lumen prior to initiation of the injection stroke. The implant length may also be reduced to accommodate an offset from the needle tip and a small amount of wire protrusion from the needle at the end of the injection stroke, to ensure complete deployment and separation from the needle.

The plunger ID affects the wire deflection in both magnitude and modality. Once the buckling mode reaches or exceeds n=2, the deflection is no longer necessarily planar and complex wire conformations, such as a helix, may occur, greatly reducing the transmission of force to the implant. Use of more complex shapes for the plunger, e.g. triangular, may enable higher force transmission at high n buckling modes, but at the cost of larger deflection. Larger deflection may also lead to slack during the initial injection stroke, followed by a potential recoil-driven acceleration of injection at the end of the stroke, limiting user control of the injection rate. Thus, the plunger inside dimensions may be as snug as possible with respect to the needle OD.

This injector concept may deploy hydrogel depots with lengths of an abnormally long plunger stroke. User depresses a plunger with an inner bore. The inner bore of the plunger houses and supports a staked push wire which progresses into a needle cannula as the plunger is depressed. The long hydrogel fibers are staged inside the needle cannula. The push wire is supported throughout the entire deployment stroke as it is advancing the fibers through the needle cannula.

In certain embodiments, the device herein (e.g., implant injector device 100) contains a sustained release biodegradable ocular implant (e.g., implant 180) comprising a hydrogel and at least about 150 µg of a tyrosine kinase inhibitor (TKI), wherein TKI particles are dispersed within the hydrogel, and wherein the implant in its dry state has a length of less than about 17 mm. In certain embodiments, the TKI is axitinib.

In certain embodiments, the sustained release biodegradable ocular is cylindrical and in its dry state has a diameter of about 0.1 mm to about 0.5 mm. In other embodiments, the implant is non-cylindrical.

In certain embodiments, the sustained release biodegradable ocular implant comprises axitinib in an amount of about 150 µg to about 1800 µg, in an amount of about 150 µg to about 1200 µg, in an amount of about 480 µg to about 750 µg or of about 160 µg to about 250 µg.

In certain embodiments, the sustained release biodegradable ocular implant in its dry state has a total weight of about 0.2 mg to about 1.5 mg, or a total weight of about 0.75 mg to 1.25 mg.

In certain embodiments, the sustained release biodegradable ocular implant is for administration into the posterior section of the eye.

In certain embodiments, the implant is an intravitreal implant.

In certain embodiments, the sustained release biodegradable ocular implant is cylindrical and in its dry state has a length of about 6 mm to about 10 mm.

In certain embodiments, the sustained release biodegradable ocular is cylindrical and in its dry state has a diameter of about 0.2 mm to about 0.4 mm.

In certain embodiments, the sustained release biodegradable ocular implant is cylindrical and in its hydrated state (after 24 hours in phosphate-buffered saline at a pH of 7.2 at 37° C.) has a length of equal to or less than about 10 mm and a diameter of equal to or less than about 0.8 mm.

In certain embodiments, the sustained release biodegradable ocular implant is cylindrical and has a ratio of the diameter in the hydrated state to the diameter in the dry state of less than about 5, or less than about 2.25.

In certain embodiments, the sustained release biodegradable ocular implant is cylindrical and has a ratio of the length in the dry state to the length in the hydrated state of greater than about 0.7, or greater than about 0.8.

In certain embodiments, the sustained release biodegradable ocular implant provides for the release of axitinib at an average rate of about 0.25 µg to about 2.5 µg per day, of about µg to about 1.5 µg per day, or of about 0.3 µg to about 0.5 µg per day, in phosphate-buffered saline at a pH of 7.2 and 37° C. for a period of 30 days under non-sink simulated physiological conditions.

In certain embodiments, the sustained release biodegradable ocular implant provides for the release of the TKI for a period of at least 3 months after administration, or a period of at least 6 months after administration, or a period of at least 9 months after administration, or a period of at least 12 months after administration, or a period of about 6 months to about 9 months after administration.

In certain embodiments, the sustained release biodegradable ocular implant biodegrades within about 2 to about 15 months, within about 4 to about 13 months, or within about 9 to about 12 months, after administration to the vitreous humor.

In certain embodiments, the hydrogel comprises a polymer network comprising one or more units of polyalkylene glycol, polyethylene glycol, polyethylene oxide, polypropylene oxide, polyvinyl alcohol, poly (vinylpyrrolidinone), polylactic acid, polylactic-co-glycolic acid, random or block copolymers or combinations or mixtures of any of these, or one or more units of polyaminoacids, glycosaminoglycans, polysaccharides, or proteins.

In certain embodiments, the hydrogel comprises polyethylene glycol (PEG) units.

In certain embodiments, the hydrogel comprises multi-arm PEG units that are the same or different, and that have a number average molecular weight of from about 10,000 to about 60,000 Daltons, or about 20,000 Daltons.

In certain embodiments, the hydrogel comprises crosslinked PEG units and the crosslinks between the PEG units include a group represented by the following formula

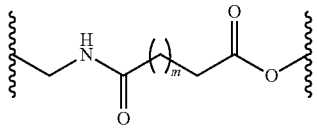

wherein m is an integer from 0 to 10, preferably m is 6.

In certain embodiments, the PEG units comprise 4-arm and/or 8-arm PEG units, or 4a20 k and 8a20 k PEG units.

In certain embodiments, the implant in its wet state contains no more than about 40% by weight TKI of the wet composition.

In certain embodiments, the implant in its dry state contains from about 25% to about 75% by weight TKI and from about 20% to about 60% by weight PEG units (dry composition).

In certain embodiments, the implant in its dry state contains from about 60% to about 75% by weight TKI and from about 21% to about 31% by weight PEG units, or contains from about 45% to about 55% by weight TKI and from about 37% to about 47% by weight PEG units (dry composition).

In certain embodiments, the implant in its dry state contains from about 200 µg to about 1000 µg TKI per mm$^3$, and preferably contains from about 500 µg to about 800 µg axitinib per mm$^3$.

In certain embodiments, the implant is an intravitreal implant and comprises from about 480 µg to about 750 µg axitinib or from about 540 µg to about 660 µg axitinib, or about 600 µg axitinib, is cylindrical and has in its dry state a length of less than or equal to 10 mm and a diameter of about 0.3 mm to about 0.4 mm, and in its hydrated state (after 24 hours in phosphate-buffered saline at a pH of 7.2 at 37° C.) has a length of from about 6 mm to about 10.5 mm and a diameter of from about 0.6 mm to about 0.8 mm, and wherein the hydrogel comprises crosslinked 4a20 k and 8a20 k PEG units, wherein the crosslinks between the PEG units include a group represented by the following formula

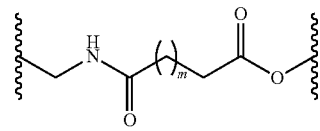

wherein m is 6.

In certain embodiments, the implant is an intravitreal implant and comprises from about 160 µg to about 250 µg axitinib, or from about 180 µg to about 220 µg axitinib, or about 200 µg axitinib, is cylindrical and has in its dry state a length of less than about 17 mm and a diameter of about 0.2 mm to about 0.3 mm, and in its hydrated state (after 24 hours in phosphate-buffered saline at a pH of 7.2 at 37° C.) has a length of from about 6.5 mm to about 8 mm and a diameter of from about 0.7 mm to about 0.8 mm, and wherein the hydrogel comprises crosslinked 4a20 k and 8a20 k PEG units, wherein the crosslinks between the PEG units include a group represented by the following formula

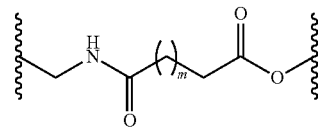

wherein m is 6.

In certain embodiments, the TKI particles have a d90 particle size of less than about 30 µm as determined by laser diffraction.

In certain embodiments, the implant is free or substantially free of antimicrobial preservatives.

In certain embodiments, the implant (e.g., implant 180) comprises a therapeutic agent. The therapeutic agent can be a prostaglandin antagonist, such as travoprost, bimatoprost or latanoprost.

In certain embodiments, the administering of the ocular implant (e.g., implant 180) via a device of the present disclosure is to treat an ocular disease.

In certain embodiments, the ocular implant (e.g., implant 180) includes an active agent.

In certain embodiments, the administering of the ocular implant (e.g., implant 180) is intravitreal or intracameral.

In certain embodiments, the ocular implant (e.g., implant 180) includes an active agent that is a tyrosine kinase inhibitor.

In certain embodiments, the ocular implant (e.g., implant 180) includes an active agent that is a tyrosine kinase inhibitor that is axitinib.

In certain embodiments, the administering of the ocular implant (e.g., implant 180) via a device of the present disclosure is to treat an ocular disease that is a back of eye disease.

In certain embodiments, the administering of the ocular implant (e.g., implant 180) via a device of the present disclosure is to treat an ocular disease that is a back of eye disease that is retinal disease.

In certain embodiments, the administering of the ocular implant (e.g., implant 180) via a device of the present disclosure is to treat an ocular disease that is age-related macular degeneration (AMD) cystoid macular edema (CME), diabetic macular edema (DME), retinal vein occlusion, posterior uveitis, diabetic retinopathy, or glaucoma.

In certain embodiments, the administering of the ocular implant (e.g., implant 180) is to an anterior chamber or a vitreous chamber.

In certain embodiments, the ocular implant (e.g., implant 180) includes an active agent that is a prostaglandin.

In certain embodiments, the ocular implant (e.g., implant 180) includes an active agent that is Travoprost.

In certain embodiments, the ocular implant (e.g., implant 180) is used to treat an ocular disease that is a front of the eye disease.

In certain embodiments, the ocular implant (e.g., implant 180) is used to treat an ocular disease that is high pressure in the eye caused by open-angle glaucoma or ocular hypertension.

Therapeutic agents also include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™) sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; EYELEA (VEGF Trap) or complement inhibitor (POT-4).

The therapeutic agent may comprise a kinase inhibitor such as one or more of BIBW 2992 (small molecule targeting EGFR/Erb2), imatinib (small molecule), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.). The therapeutic agent may comprises antibody drugs, e.g. bevacizumab, trastuzumab, cetuximab, and panitumumab.

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antioxidants, antibiotics, pain relievers, inhibitors of vascular endothelial growth factor (VEGF), chemotherapeutics, anti-viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides of various molecular weights. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure-open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure-open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, permeation agents for an eye, etc.

The agent may be treatment of a back of the eye disease, e.g., wherein the back of the eye disease is age-related macular degeneration (AMD) cystoid macular edema (CME), diabetic macular edema (DME), posterior uveitis, and diabetic retinopathy, or glaucoma.

The agents may be, e.g., an agent comprises anti-VEGF, blocks VEGFR1, blocks VEGFR2, blocks VEGFR3, anti-PDGF, anti-PDGF-R blocks PDGFRβ, an anti-angiogenic agent, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinibn gefinitib, toceranib, Erlotinib, Lapatinib, Nilotinib, Bosutinib Neratinib, lapatinib, Vatalanib, comprises low-soluble prostaglandin analogues for glaucoma, nepafenac, macrolides, rapamycin, sirolimus, tacrolimus, or serves to block mTOR receptors for AMD (also known as choroidal neovascularization (CNV). mTOR refers to mammalian target of rapamycin. Agents may be, e.g., moxifloxacin, dexamethasone, travoprost, steroids, fluoroquinolones, prostaglandin analogs, prostamides.

Ocular diseases include ocular pathologies, with hyphema, ocular hypertension, and glaucoma being conditions for treatment with an anterior chamber depot. Many agents are suitable for ocular delivery, e.g., NSAIDs, steroids, anti-glaucoma drugs, antivirals, antibiotics, mydriatics, and antifungals administered via intracameral injections.

Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other ocular conditions may be provided by delivery of agents from an implant.

The preceding description sets forth numerous specific details such as examples of specific systems, components, methods, and so forth in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

Reference throughout this specification to "one embodiment," "an embodiment," or "some embodiments" means that a particular feature, structure, or characteristic described in connection with the embodiment is included in at least one embodiment. Thus, the appearances of the phrase "in one embodiment," "in an embodiment," or "in some embodiments" in various places throughout this specification are not necessarily all referring to the same embodiment. In addition, the term "or" is intended to mean an inclusive "or" rather than an exclusive "or." When the term "about" or "approximately" is used herein, this is intended to mean that the nominal value presented is precise within ±10%.

Although the operations of the methods herein are shown and described in a particular order, the order of operations of each method may be altered so that certain operations may be performed in an inverse order so that certain operations may be performed, at least in part, concurrently with other operations. In another embodiment, instructions or sub-operations of distinct operations may be in an intermittent and/or alternating manner.

It is understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A system comprising:
    a first assembly comprising:
        a body forming a first interior volume;
        a plunger comprising a first end of the plunger disposed within the first interior volume and a second end of the plunger disposed outside the body, the second end being opposite the first end;
        a wire comprising a first end of the wire directly connected to the first end of the plunger; and
        a plunger clip configured to interface with the plunger and the body to prevent actuation of the plunger via the second end of the plunger; and
    a second assembly comprising:
        a cowl forming a second interior volume;
        a needle comprising a hub and a shaft, a first end of the shaft being connected to the hub, the hub being disposed within the second interior volume, wherein the shaft is configured to receive an implant, wherein the implant is to be deployed from the shaft responsive to the plunger clip being removed and the plunger being actuated by a first threshold force that is greater than a friction force of one or more living hinges of the body against the plunger; and
        a cowl cap disposed partially within the hub to secure the implant in the shaft.

2. The system of claim 1, wherein the implant is to be deployed from the shaft via the wire responsive to removal of the plunger clip and the actuation of the plunger via the second end of the plunger.

3. The system of claim 1 further comprising a biocompatible material tip coupled to a second end of the shaft of the needle, wherein the implant is secured in the shaft between the cowl cap and the biocompatible material tip, wherein the biocompatible material tip is configured to at least partially dissolve within a user to allow the implant to be deployed into the user.

4. The system of claim 1, wherein the body comprises a first body half having a pattern of staggered clips and staggered recesses, wherein the body further comprises a second body half having the pattern of the staggered clips and the staggered recesses, wherein the first body half and the second body half are configured to interconnect with each other via the staggered clips and the staggered recesses.

5. The system of claim 1, wherein the cowl comprises a first cowl half and a second cowl half configured to interconnect with each other.

6. The system of claim 1, wherein the plunger comprises a protrusion configured to actuate the one or more living hinges of the body responsive to the first threshold force, and wherein the protrusion prevents the plunger from being removed from the body responsive to actuation of the plunger without a second threshold force.

7. The system of claim 1, wherein the cowl comprises one or more clips configured to secure to recesses formed by a end of the body responsive to the cowl cap being removed from the hub, and wherein the wire is configured to insert into a portion of the shaft responsive to the one or more clips securing to the recesses.

8. The system of claim 1, wherein the plunger clip comprises a curved profile to provide a friction fit on the body.

9. The system of claim 1, wherein the second assembly further comprises a needle shield configured to secure to the cowl to be disposed around at least a portion of the shaft.

10. An implant injector device comprising:
    a body forming a first interior volume;
    a plunger comprising a first end of the plunger disposed within the first interior volume and a second end of the plunger disposed outside the body, the second end being opposite the first end;
    a wire comprising a first end of the wire directly connected to the first end of the plunger;
    a plunger clip configured to interface with the plunger and the body to prevent actuation of the plunger via the second end of the plunger, wherein the plunger clip comprises a curved profile to provide a friction fit on the body; and
    a shaft coupled to the body, wherein the shaft is configured to receive an implant, wherein the implant is to be deployed from the shaft via the wire responsive to removal of the plunger clip and the actuation of the plunger by a first threshold force that is greater than a friction force of one or more living hinges of the body against the plunger.

11. The implant injector device of claim 10 further comprising a biocompatible material tip coupled to an end of the shaft, wherein the biocompatible material tip is configured to at least partially dissolve within a user to allow the implant to be deployed into the user.

12. The implant injector device of claim 10, wherein the body comprises a first body half having a pattern of staggered clips and staggered recesses, wherein the body further comprises a second body half having the pattern of the staggered clips and the staggered recesses, wherein the first body half and the second body half are configured to interconnect with each other via the staggered clips and the staggered recesses.

13. The implant injector device of claim 10 further comprising:
a cowl forming a second interior volume;
a needle comprising a hub and the shaft, wherein a first end of the shaft is connected to the hub, the hub being disposed within the second interior volume; and
a cowl cap disposed partially within the hub to secure the implant in the shaft.

14. The implant injector device of claim 13, wherein:
a first assembly comprises the body, the plunger, the wire, and the plunger clip; and
a second assembly comprises the cowl, the needle, and the cowl cap.

15. The implant injector device of claim 10, wherein the first threshold force causes the actuation of the plunger via the second end of the plunger.

16. The implant injector device of claim 15, wherein the plunger comprises a protrusion configured to actuate the one or more living hinges responsive to the first threshold force, and wherein the protrusion prevents the plunger from being removed from the body responsive to actuation of the plunger without a second threshold force.

17. The implant injector device of claim 10, comprising an implant disposed within the shaft, wherein the implant comprises an active agent.

18. The implant injector device of claim 17, wherein the active agent is a tyrosine kinase inhibitor.

19. The implant injector device of claim 18, wherein the tyrosine kinase inhibitor is axitinib.

20. A kit comprising:
a first enclosure to house a first assembly, the first assembly comprising:
a body forming a first interior volume;
a plunger comprising a first end of the plunger disposed within the first interior volume and a second end of the plunger disposed outside the body, the second end being opposite the first end;
a wire comprising a first end of the wire directly connected to the first end of the plunger; and
a plunger clip configured to interface with the plunger and the body to prevent actuation of the plunger via the second end of the plunger; and
a second enclosure to house a second assembly, the second assembly comprising:
a cowl forming a second interior volume;
a needle comprising a hub and a shaft, a first end of the shaft being connected to the hub, the hub being disposed within the second interior volume; and
a cowl cap disposed partially within the hub, wherein an implant is to be deployed from the shaft responsive to the plunger clip being removed and the plunger being actuated by a first threshold force that is greater than a friction force of one or more living hinges of the body against the plunger.

21. The kit of claim 20, wherein the second assembly further comprises the implant disposed within the shaft.

22. The kit of claim 21, wherein the implant comprises an active agent.

23. The kit of claim 22, wherein the active agent is a tyrosine kinase inhibitor.

24. The kit of claim 23, wherein the tyrosine kinase inhibitor is axitinib.

25. A system comprising:
a first assembly comprising:
a body forming a first interior volume;
a plunger comprising a first end of the plunger disposed within the first interior volume and a second end of the plunger disposed outside the body, the second end being opposite the first end;
a wire comprising a first end of the wire directly connected to the first end of the plunger; and
a plunger clip configured to interface with the plunger and the body to prevent actuation of the plunger via the second end of the plunger;
a second assembly comprising:
a cowl forming a second interior volume;
a needle comprising a hub and a shaft, a first end of the shaft being connected to the hub, the hub being disposed within the second interior volume; and
a cowl cap disposed partially within the hub; and
an implant disposed within the shaft, wherein the implant comprises an active agent, and wherein the cowl cap disposed partially within the hub secures the implant in the shaft, and wherein the implant is to be deployed from the shaft responsive to the plunger clip being removed and the plunger being actuated by a first threshold force that is greater than a friction force of one or more living hinges of the body against the plunger.

26. The system of claim 25, wherein the active agent is a tyrosine kinase inhibitor.

27. The system of claim 26, wherein the tyrosine kinase inhibitor is axitinib.

28. A system comprising: a first assembly comprising: a body forming a first interior volume; a plunger comprising a first end of the plunger disposed within the first interior volume and a second end of the plunger disposed outside the body, the second end being opposite the first end; a wire comprising a first end of the wire directly connected to the first end of the plunger; and a plunger clip configured to interface with the plunger and the body to prevent actuation of the plunger via the second end of the plunger; and a second assembly comprising:
a cowl forming a second interior volume; a needle comprising a hub and a shaft, a first end of the shaft being connected to the hub, the hub being disposed within the second interior volume, wherein the shaft is configured to receive an implant;
and a cowl cap disposed partially within the hub to secure the implant in the shaft, wherein the cowl comprises one or more clips configured to secure to recesses formed by an end of the body responsive to the cowl cap being removed from the hub, and wherein the wire is configured to insert into a portion of the shaft responsive to the one or more clips securing to the recesses.

29. A system comprising:
a first assembly comprising:
- a body forming a first interior volume;
- a plunger comprising a first end of the plunger disposed within the first interior volume and a second end of the plunger disposed outside the body, the second end being opposite the first end;
- a wire comprising a first end of the wire directly connected to the first end of the plunger; and
- a plunger clip configured to interface with the plunger and the body to prevent actuation of the plunger via the second end of the plunger; and a second assembly comprising:
- a cowl forming a second interior volume;
- a needle comprising a hub and a shaft, a first end of the shaft being connected to the hub, the hub being disposed within the second interior volume, wherein the shaft is configured to receive an implant;
- a cowl cap disposed partially within the hub to secure the implant in the shaft; and
- a needle shield configured to secure to the cowl to be disposed around at least a portion of the shaft.

* * * * *